US011723577B2

(12) United States Patent
Pedalty et al.

(10) Patent No.: US 11,723,577 B2
(45) Date of Patent: Aug. 15, 2023

(54) VISUALIZATION OF ARRHYTHMIA DETECTION BY MACHINE LEARNING

(71) Applicant: Medtronic, Inc., Minneapolis, MN (US)

(72) Inventors: Lindsay A. Pedalty, Minneapolis, MN (US); Niranjan Chakravarthy, Singapore (SG); Rodolphe Katra, Blaine, MN (US); Tarek D. Haddad, Minneapolis, MN (US); Andrew Radtke, Minneapolis, MN (US); Siddharth Dani, Minneapolis, MN (US); Donald R. Musgrove, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 308 days.

(21) Appl. No.: 16/850,749

(22) Filed: Apr. 16, 2020

(65) Prior Publication Data
US 2020/0352462 A1 Nov. 12, 2020

Related U.S. Application Data

(60) Provisional application No. 62/843,730, filed on May 6, 2019.

(51) Int. Cl.
*A61B 5/361* (2021.01)
*A61B 5/00* (2006.01)
(Continued)

(52) U.S. Cl.
CPC ............. *A61B 5/361* (2021.01); *A61B 5/316* (2021.01); *A61B 5/322* (2021.01); *A61B 5/346* (2021.01);
(Continued)

(58) Field of Classification Search
None
See application file for complete search history.

(56) References Cited

U.S. PATENT DOCUMENTS

| 4,458,691 A | 7/1984 | Netravali |
| 6,212,428 B1 | 4/2001 | Hsu et al. |

(Continued)

FOREIGN PATENT DOCUMENTS

| CN | 108030488 A | 5/2018 |
| EP | 1218060 B1 | 7/2002 |

(Continued)

OTHER PUBLICATIONS

Bresnick, "Machine Learning Algorithm Outperforms Cardiologists Reading EKGs," Analytics in Action News, HealthITAnalytics.com, Jul. 12, 2017; https://healthitanalytics.com/news/machine-learning-algorithm-outperforms-cardiologists-reading-ekgs (Year: 2017).*

(Continued)

*Primary Examiner* — Kennedy Schaetzle
(74) *Attorney, Agent, or Firm* — Shumaker & Sieffert, P.A.

(57) ABSTRACT

Techniques are disclosed for explaining and visualizing an output of a machine learning system that detects cardiac arrhythmia in a patient. In one example, a computing device receives cardiac electrogram data sensed by a medical device. The computing device applies a machine learning model, trained using cardiac electrogram data for a plurality of patients, to the received cardiac electrogram data to determine, based on the machine learning model, that an episode of arrhythmia has occurred in the patient and a level of confidence in the determination that the episode of arrhythmia has occurred in the patient. In response to determining that the level of confidence is greater than a predetermined threshold, the computing device displays, to a user, a portion of the cardiac electrogram data, an indica- (Continued)

tion that the episode of arrhythmia has occurred, and an indication of the level of confidence that the episode of arrhythmia has occurred.

31 Claims, 18 Drawing Sheets

(51) Int. Cl.
  A61B 5/316 (2021.01)
  A61B 5/322 (2021.01)
  A61B 5/352 (2021.01)
  A61B 5/363 (2021.01)
  A61B 5/346 (2021.01)

(52) U.S. Cl.
  CPC ............. *A61B 5/352* (2021.01); *A61B 5/363* (2021.01); *A61B 5/7264* (2013.01); *A61B 5/742* (2013.01); *A61B 5/7405* (2013.01)

(56) References Cited

U.S. PATENT DOCUMENTS

| | | |
|---|---|---|
| 6,308,094 B1 | 10/2001 | Shusterman et al. |
| 6,594,523 B1 | 7/2003 | Levine |
| 8,103,346 B2 | 1/2012 | Mass et al. |
| 8,521,281 B2 | 8/2013 | Patel et al. |
| 9,183,351 B2 | 11/2015 | Shusterman |
| 9,483,529 B1 | 11/2016 | Pasoi et al. |
| 9,585,590 B2 | 3/2017 | McNair |
| 9,743,890 B2* | 8/2017 | Lord ................ A61B 5/021 |
| 9,775,559 B2 | 10/2017 | Zhang et al. |
| 10,463,269 B2 | 11/2019 | Boleyn et al. |
| 10,744,334 B2 | 8/2020 | Perschbacher et al. |
| 2002/0016550 A1 | 2/2002 | Sweeney et al. |
| 2002/0123768 A1 | 9/2002 | Gilkerson et al. |
| 2006/0247709 A1 | 11/2006 | Gottesman et al. |
| 2009/0259269 A1 | 10/2009 | Brown |
| 2010/0179444 A1 | 7/2010 | O'Brien et al. |
| 2010/0268103 A1 | 10/2010 | McNamara et al. |
| 2010/0280841 A1 | 11/2010 | Dong et al. |
| 2011/0270109 A1 | 11/2011 | Zhang et al. |
| 2012/0004563 A1 | 1/2012 | Kim et al. |
| 2012/0209126 A1 | 8/2012 | Amos et al. |
| 2013/0274524 A1 | 10/2013 | Dakka et al. |
| 2013/0274624 A1 | 10/2013 | Mahajan et al. |
| 2014/0257063 A1 | 9/2014 | Ong et al. |
| 2015/0164349 A1 | 6/2015 | Gopalakrishnan et al. |
| 2015/0216435 A1 | 8/2015 | Bokan et al. |
| 2015/0265217 A1* | 9/2015 | Penders ................ A61B 5/681 600/300 |
| 2016/0022164 A1 | 1/2016 | Brockway et al. |
| 2016/0135706 A1 | 5/2016 | Sullivan et al. |
| 2016/0192853 A1* | 7/2016 | Bardy ................ A61B 5/333 600/382 |
| 2016/0220137 A1 | 8/2016 | Mahajan et al. |
| 2016/0232280 A1 | 8/2016 | Apte et al. |
| 2017/0095673 A1 | 4/2017 | Ludwig et al. |
| 2017/0105683 A1 | 4/2017 | Xue |
| 2017/0156592 A1 | 6/2017 | Fu |
| 2017/0196458 A1 | 7/2017 | Ternes et al. |
| 2017/0265765 A1 | 9/2017 | Baumann et al. |
| 2017/0290550 A1 | 10/2017 | Perschbacher et al. |
| 2017/0347894 A1 | 12/2017 | Bhushan et al. |
| 2017/0354365 A1 | 12/2017 | Zhou |
| 2018/0089763 A1 | 3/2018 | Okazaki |
| 2018/0146874 A1* | 5/2018 | Walker ................ A61B 5/358 |
| 2018/0146929 A1 | 5/2018 | Joo et al. |
| 2018/0206721 A1 | 7/2018 | Zhang |
| 2018/0233227 A1 | 8/2018 | Galloway et al. |
| 2018/0272147 A1 | 9/2018 | Freeman et al. |
| 2018/0279891 A1 | 10/2018 | Miao et al. |
| 2018/0310892 A1 | 11/2018 | Perschbacher et al. |
| 2019/0008461 A1 | 1/2019 | Gupta et al. |
| 2019/0029552 A1 | 1/2019 | Perschbacher et al. |
| 2019/0038148 A1 | 2/2019 | Valys et al. |
| 2019/0038149 A1 | 2/2019 | Gopalakrishnan et al. |
| 2019/0090774 A1 | 3/2019 | Yang et al. |
| 2019/0122097 A1 | 4/2019 | Shibahara et al. |
| 2019/0209022 A1 | 7/2019 | Sobol et al. |
| 2019/0272920 A1 | 9/2019 | Teplitzky |
| 2019/0275335 A1 | 9/2019 | Volpe et al. |
| 2019/0343415 A1 | 11/2019 | Saha et al. |
| 2019/0365342 A1 | 12/2019 | Ghaffarzadegan et al. |
| 2019/0378620 A1* | 12/2019 | Sarén ................ G16H 50/30 |
| 2020/0100693 A1 | 4/2020 | Velo |
| 2020/0108260 A1 | 4/2020 | Haddad et al. |
| 2020/0178825 A1 | 6/2020 | Weijia et al. |
| 2020/0288997 A1 | 9/2020 | Shute et al. |
| 2020/0352466 A1 | 11/2020 | Chakravarthy et al. |
| 2021/0137384 A1 | 5/2021 | Robinson et al. |
| 2021/0169736 A1 | 6/2021 | Wijshoff et al. |
| 2021/0204858 A1* | 7/2021 | Attia ................ A61B 5/7264 |
| 2021/0345865 A1* | 11/2021 | Spillinger .......... A61B 1/00016 |

FOREIGN PATENT DOCUMENTS

| | | |
|---|---|---|
| EP | 2427105 A1 | 3/2012 |
| WO | 2010129447 A1 | 11/2010 |
| WO | 2013/160538 A1 | 10/2013 |
| WO | 2017072250 A1 | 5/2017 |
| WO | 2017091736 A1 | 6/2017 |
| WO | 2018119316 A1 | 6/2018 |
| WO | 2020049267 A1 | 3/2020 |

OTHER PUBLICATIONS

International Search Report and Written Opinion of International Application No. PCT/US2020/028721, dated Jul. 8, 2020, 11 pp.
U.S. Appl. No. 16/832,732, filed Mar. 27, 2020 by Chakravarthy et al.
U.S. Appl. No. 16/845,996, filed Apr. 10, 2020 by Haddad et al.
U.S. Appl. No. 16/851,603, filed Apr. 17, 2020 by Chakravarthy et al.
U.S. Appl. No. 16/850,699, filed Apr. 16, 2020 by Chakravarthy et al.
U.S. Appl. No. 17/373,480, filed Jul. 12, 2021, naming inventors Chakravarthy et al.
U.S. Appl. No. 17/377,785, filed Jul. 16, 2021, Pedalty et al.
U.S. Appl. No. 17/389,831, filed Jul. 30, 2021, by Haddad et al.
U.S. Appl. No. 17/377,763, filed Jul. 16, 2021, naming inventors Chakravarthy et al.
Isin et al., "Cardiac Arrhythmia Detection Using Deep Learning," Procedia Computer Science vol. 120, 2017 (Applicant points out, in accordance with MPEP 609.04(a), that the year of publication, 2017, is sufficiently earlier than the effective U.S. filing date, so that the particular month of publication is not in issue.) pp. 268-275.
Arrobo et al., "An Innovative Wireless Cardiac Rhythm Management (iCRM) System," Computer Science, 2014 Wireless Telecommunications Symposium, Jun. 2014, 5 pp.
Swerdlow et al., "Troubleshooting Implanted Cardioverter Defibrillator Sensing Problems I," Advances in Arrhythmia and Electrophysiology, vol. 7, No. 6, Dec. 2014, pp. 1237-1261.
Wartzek et al., "ECG on the Road: Robust and Unobtrusive Estimation of Heart Rate," IEEE Transactions on Biomedical Engineering, vol. 58, No. 11, Nov. 2011, pp. 3112-3120.
Anonymous, "Receiver Operating Characteristic—Wikipedia," Mar. 20, 2019, Retrieved from the Internet: URL: https://en.wikipedia.org/w/index.php?title=Receiver_operating_characteristic&oldis-888671034#History, 12 pp.
Habibzadeh et al., "On Determining the Most Appropriate Test Cut-Off Value: the Case of Tests with Continuous Results," Biochemia Medica, Oct. 15, 2016, pp. 297-307.
"Visualize Features of a Convolutional Neural Network," Matlab & Simulink, retrieved from https://www.mathworks.com/help/deeplearning/examples/visualize-features-of-a-convolutional-neural-network.html, Sep. 11, 2019, 7 pp.
U.S. Appl. No. 17/383,170, filed Jul. 22, 2021, naming inventors Haddad et al.

(56) References Cited

OTHER PUBLICATIONS

Notice of Allowance from U.S. Appl. No. 17/377,785, dated Sep. 15, 2021, 10 pp.

"Visualize Features of a Convolutional Neural Network," Matlab & Simulink, Mar. 15, 2018, 9 pp.

"Classify ECG Signals Using Long Short-Term Memory Networks," Matlab, retrieved from https://www.mathworks.com/help/signal/examples/classify-ecg-signals-using-long-short-term-memory-networks.html, Nov. 2, 2018, 19 pp.

Fawaz et al., "Deep learning for time series classification: a review," Irirmas, Universite Haute Alsace, Dec. 7, 2018, 53 pp.

Kelwade et al., "Prediction of Cardiac Arrhythmia using Artificial Neural Network," International Journal of Computer Applications (0975-8887), vol. 115—No. 20, Apr. 2015, 6 pp.

Lau et al., "Connecting the Dots: From Big Data to Healthy Heart," Circulation, vol. 134, No. 5, Aug. 2, 2016, 5 pp.

Schwab et al., "Beat by Beat: Classifying Cardiac Arrhythmias with Recurrent Neural Networks," 2017 Computing in Cardiology (CinC), vol. 44, Oct. 24, 2017, 4 pp.

U.S. Appl. No. 16/593,739, filed Oct. 4, 2019 by Haddad et al.

U.S. Appl. No. 62/843,717, filed May 6, 2019 by Chakravarthy et al.

U.S. Appl. No. 62/843,738, filed May 6, 2019 by Chakravarthy et al.

U.S. Appl. No. 62/843,762, filed May 6, 2019 by Chakravarthy et al.

U.S. Appl. No. 62/843,786, filed May 6, 2019 by Haddad et al.

Andersen et al., "A deep learning approach for real-time detection of atrial fibrillation," Expert Systems with Applications, Elsevier, available online Aug. 14, 2018, 9 pp.

Madani et al., "Fast and accurate view classification of echocardiograms using deep learning," NPJ Digital Medicine, vol. 1, No. 6 Mar. 21, 2018, 8 pp.

Schirrmeister et al., "Deep learning with convolutional neural networks for brain mapping and decoding of movement-related information from the human EEG," arXiv:170.05051v1, Mar. 16, 2017, 58 pp.

U.S. Appl. No. 16/850,833, filed Apr. 16, 2020 by Dani et al.

U.S. Appl. No. 16/851,500, filed Apr. 17, 2020 by Musgrove et al.

International Preliminary Report on Patentability from International Application No. PCT/US2020/028721, dated Nov. 18, 2021, 6 pp.

Notice of Allowance from U.S. Appl. No. 17/377,785 dated Oct. 26, 2022, 6 pp.

Response to Final Office Action dated Aug. 8, 2022 from U.S. Appl. No. 17/377,785, filed Oct. 5, 2022, 15 pp.

Witten et al., "Data mining: Practical Machine Learning Tools and Techniques," Third Edition, Morgan Kaufmann, Feb. 3, 2011, 665 pp.

Chen et al., "Electrocardiogram Recognition Based on Variational AutoEncoder," Machine Learning and Biometrics, IntechOpen, Aug. 29, 2018, pp. 71-90.

Final Office Action from U.S. Appl. No. 17/377,785 dated Aug. 8, 2022, 13 pp.

Office Action from U.S. Appl. No. 17/377,785, dated Mar. 23, 2022, 9 pp.

Response to Office Action dated Mar. 23, 2022, from U.S. Appl. No. 17/377,785, filed Jun. 23, 2022, 15 pp.

\* cited by examiner

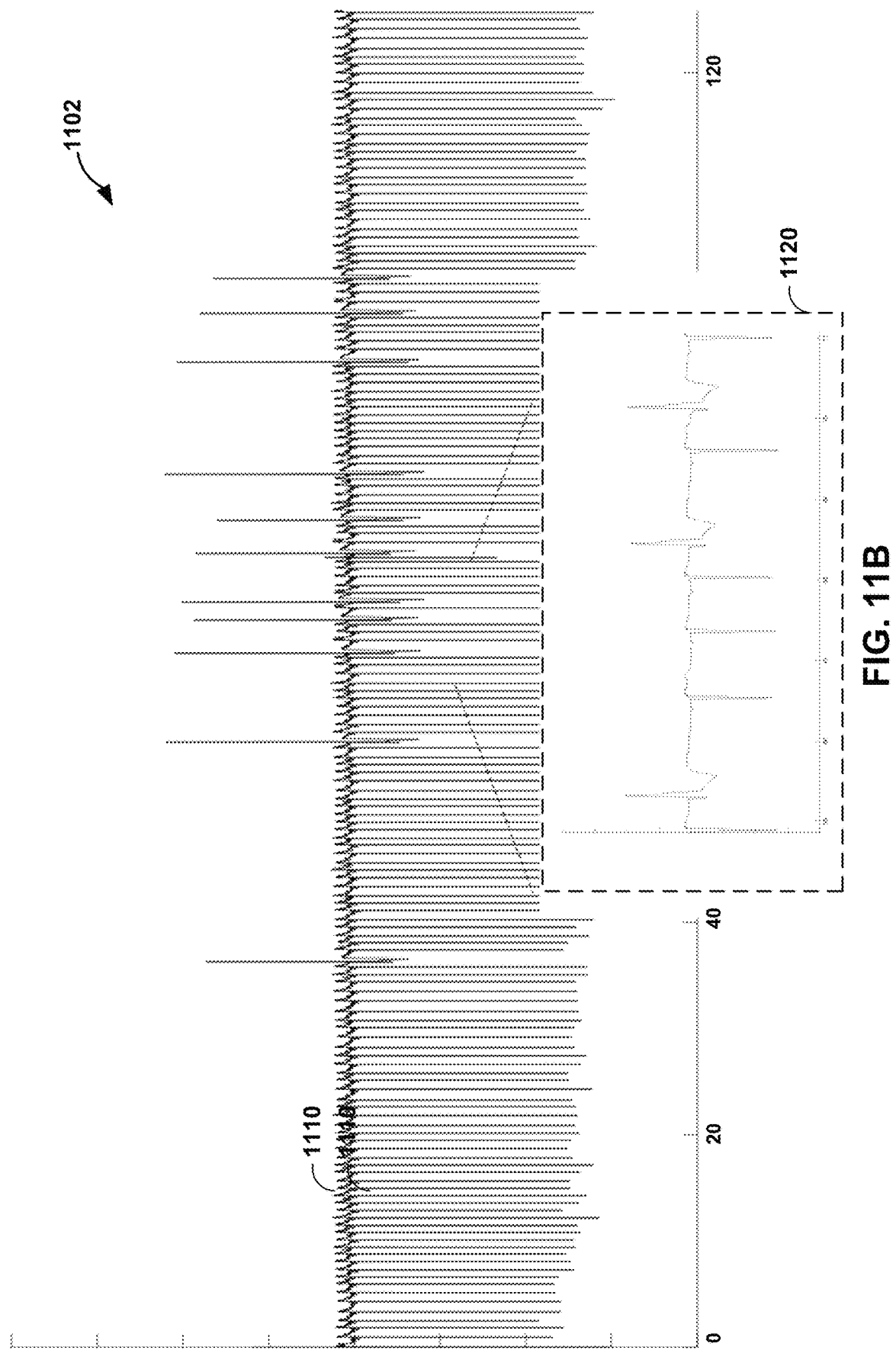

VISUALIZATION OF ARRHYTHMIA DETECTION BY MACHINE LEARNING

This application claims the benefit of U.S. Provisional Application No. 62/843,730 which was filed on May 6, 2019. The entire content of Application No. 62/843,730 is incorporated herein by reference.

FIELD

This disclosure generally relates to medical devices.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. Consequently, sudden cardiac death (SCD) may result in a matter of minutes.

In patients with a high risk of ventricular fibrillation, the use of an implantable medical device (IMD), such as an implantable cardioverter defibrillator (ICD), has been shown to be beneficial at preventing SCD. An ICD is a battery powered electrical shock device, that may include an electrical housing electrode (sometimes referred to as a can electrode), that is typically coupled to one or more electrical lead wires placed within the heart. If an arrhythmia is sensed, the ICD may send a pulse via the electrical lead wires to shock the heart and restore its normal rhythm. Some ICDs have been configured to attempt to terminate detected tachyarrhythmias by delivery of anti-tachycardia pacing (ATP) prior to delivery of a shock. Additionally, ICDs have been configured to deliver relatively high magnitude post-shock pacing after successful termination of a tachyarrhythmia with a shock, in order to support the heart as it recovers from the shock. Some ICDs also deliver bradycardia pacing, cardiac resynchronization therapy (CRT), or other forms of pacing.

Other types of medical devices may be used for diagnostic purposes. For instance, an implanted or non-implanted medical device may monitor a patient's heart. A user, such as a physician, may review data generated by the medical device for occurrences of cardiac arrhythmias, e.g., atrial or ventricular tachyarrhythmia, or asystole. The user may diagnose a medical condition of the patient based on the identified occurrences of the cardiac arrhythmias.

SUMMARY

In accordance with the techniques of the disclosure, a medical device system is set forth herein that explains and visualizes an output of a machine learning system that detects cardiac arrhythmia in a patient. Machine learning systems may provide powerful tools for detecting and classifying episodes of arrhythmia in a patient. However, the foundations for the conclusions drawn by such machine learning systems may be difficult to convey to a non-expert. Techniques are disclosed herein for simplifying the conclusions drawn by a machine learning system with respect to the detection of cardiac arrhythmia in a patient and presenting such information in a manner that is comprehensible to users of differing ability, including subject matter experts and non-experts alike.

In one example, a computing device receives cardiac electrogram data sensed by a medical device. The computing device applies a machine learning model, trained using cardiac electrogram data for a plurality of patients, to the received cardiac electrogram data to determine, based on the machine learning model, that an episode of arrhythmia has occurred in the patient and a level of confidence in the determination that the episode of arrhythmia has occurred in the patient. In response to determining that the level of confidence is greater than a predetermined threshold, the computing device displays, to a user, a portion of the cardiac electrogram data, an indication that the episode of arrhythmia has occurred, and an indication of the level of confidence that the episode of arrhythmia has occurred. In some examples, the computing device provides more detailed information to advanced users and less detailed information to basic users.

In another example, the computing device receives cardiac electrogram data sensed by the medical device and a selection of an arrhythmia type from a user. The computing device applies the machine learning model to the received cardiac electrogram data to determine, based on the machine learning model, that an episode of arrhythmia of the selected type has occurred in the patient and a level of confidence in the determination that the episode of arrhythmia of the selected type has occurred. The computing device outputs, for display, at least a portion of the cardiac electrogram data, a first indication that the episode of arrhythmia of the selected type has occurred in the patient, and a second indication of the level of confidence that the episode of arrhythmia of the selected type has occurred in the patient.

The techniques of the disclosure may provide specific improvements to the field of machine learning systems that perform cardiac arrhythmia detection and classification. For example, the techniques disclosed herein may allow for more clear explainability and visualization of the analysis performed by such machine learning systems. Further, the techniques described herein may allow for quick and patient-specific interpretation of cardiac electrogram data for use by users of many different skill levels. The techniques disclosed herein may reduce the amount of training required by users to make use of conclusions provided by machine learning systems that perform cardiac arrhythmia detection and classification, as well as enable the use of such machine learning systems in a wider variety of systems. Accordingly, the techniques disclosed herein may enable more accurate and faster diagnosis and classification of cardiac arrhythmia in patients, while reducing the amount of expertise required by clinicians to diagnose and provide therapy for such cardiac arrhythmia.

In one example, this disclosure describes a method comprising: receiving, by a computing device comprising processing circuitry and a storage medium, cardiac electrogram data sensed by a medical device; applying, by the computing device, a machine learning model, trained using cardiac electrogram data for a plurality of patients, to the received cardiac electrogram data to: determine, based on the machine learning model, that an episode of arrhythmia has occurred in the patient; and determine a level of confidence in the determination that the episode of arrhythmia has occurred in the patient; determining that the level of confidence in the determination that the episode of arrhythmia has occurred in the patient is greater than a predetermined threshold; and in response to determining that the level of confidence is greater than the predetermined threshold, outputting, by the computing device and for display to a user, at least a portion of the cardiac electrogram data, a first indication that the episode of arrhythmia has occurred in the patient, and a second indication of the level of confidence that the episode of arrhythmia has occurred in the patient.

In another example, this disclosure describes a method comprising: receiving, by a computing device comprising processing circuitry and a storage medium, cardiac electrogram data sensed by a medical device; receiving, from the user, a selection of an arrhythmia type; applying, by the computing device, a machine learning model, trained using cardiac electrogram data for a plurality of patients, to the received cardiac electrogram data to: determine, based on the machine learning model, that an episode of arrhythmia of the selected type has occurred in the patient; and determine a level of confidence in the determination that the episode of arrhythmia of the selected type has occurred in the patient; and outputting, by the computing device and for display to a user, at least a portion of the cardiac electrogram data, a first indication that the episode of arrhythmia of the selected type has occurred in the patient, and a second indication of the level of confidence that the episode of arrhythmia of the selected type has occurred in the patient.

In another example, this disclosure describes a computing device comprising: a storage medium; and processing circuitry operable coupled to the storage medium and configured to: receive cardiac electrogram data sensed by a medical device; apply a machine learning model, trained using cardiac electrogram data for a plurality of patients, to the received cardiac electrogram data to: determine, based on the machine learning model, that an episode of arrhythmia has occurred in the patient; and determine a level of confidence in the determination that the episode of arrhythmia has occurred in the patient; determine that the level of confidence in the determination that the episode of arrhythmia has occurred in the patient is greater than a predetermined threshold; and in response to determining that the level of confidence is greater than the predetermined threshold, output, for display to a user, at least a portion of the cardiac electrogram data, a first indication that the episode of arrhythmia has occurred in the patient, and a second indication of the level of confidence that the episode of arrhythmia has occurred in the patient.

In another example, this disclosure describes a computing device comprising: a storage medium; and processing circuitry operable coupled to the storage medium and configured to: receive cardiac electrogram data sensed by a medical device; receive, from a user, a selection of an arrhythmia type; apply a machine learning model, trained using cardiac electrogram data for a plurality of patients, to the received cardiac electrogram data to: determine, based on the machine learning model, that an episode of arrhythmia of the selected type has occurred in the patient; and determine a level of confidence in the determination that the episode of arrhythmia of the selected type has occurred in the patient; and output, for display to a user, at least a portion of the cardiac electrogram data, a first indication that the episode of arrhythmia of the selected type has occurred in the patient, and a second indication of the level of confidence that the episode of arrhythmia of the selected type has occurred in the patient.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

FIGS. 11A-11C are illustrations depicting another example display for visualizing cardiac electrogram data of a patient by a medical device in accordance with the techniques of the disclosure.

Like reference characters refer to like elements throughout the figures and description.

DETAILED DESCRIPTION

Machine learning systems, such as deep learning and artificial intelligence (AI), that perform arrhythmia detection provide a flexible platform to develop algorithms with different objectives. For example, machine learning systems may be used to detect atrial fibrillation (AF) segments, detect the presence of AF, or detect other types of cardiac arrhythmia. Further, such machine learning systems may be implemented without expert design and feature engineering that may be required by other techniques, such as feature delineation. However, the conclusions drawn by such machine learning systems, as well as the data drawn upon to make such conclusions, may be difficult to explain, hindering evaluation of the performance of the machine learning system.

Techniques are disclosed for explaining and visualizing an output of a machine learning system that detects cardiac arrhythmia in a patient. The techniques of the disclosure may allow for a medical device system to explain the arrhythmia classification by a machine learning model. For example, a system as described below may provide explainability and interpretability of a machine learning system that performs arrhythmia detection. Furthermore, a medical device system as described herein may present arrhythmias detected by the machine learning system for quick and patient-specific interpretation, and present such detected arrhythmias to a variety of end-users who may have different levels of familiarity and expertise with interpretation of cardiac electrogram data. Such a medical device system as described herein may provide clear explainability and simple arrhythmia visualization of a machine learning system, which may be useful as consumer and medical devices that can collect and display cardiac electrogram data proliferate.

Figure 1:
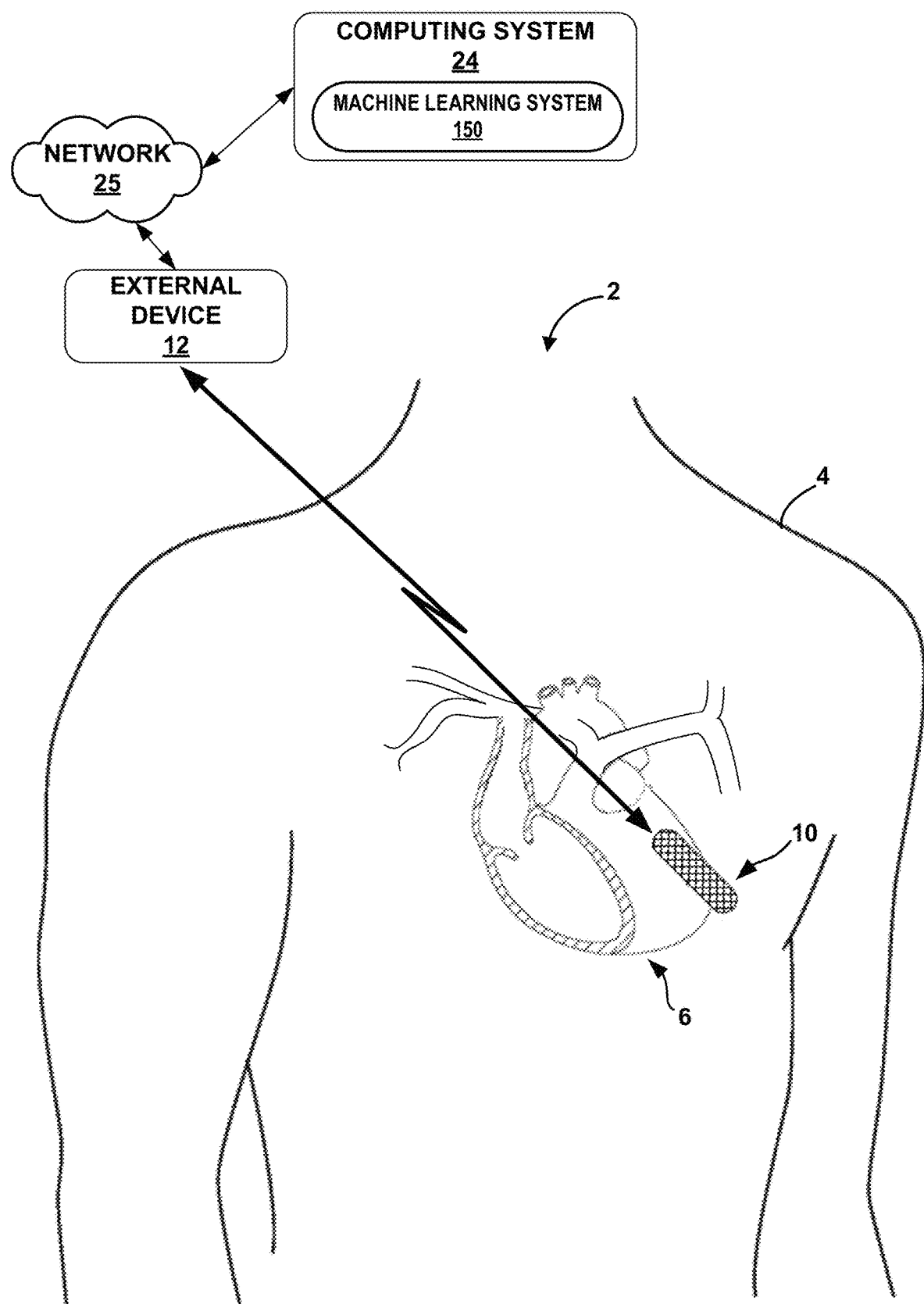
FIG. 1 is a conceptual drawing illustrating an example of a medical device system for explaining detection and classification of cardiac arrhythmia including an implantable medical device and an external device in conjunction with a patient in accordance with the techniques of the disclosure.

FIG. 1 is a conceptual drawing illustrating an example medical device system 2 for explaining detection and classification of cardiac arrhythmia in a heart 6 of patient 4 including IMD 10 and external device 12 in conjunction with a patient in accordance with the techniques of the disclosure. In some examples, IMD 10 is a leadless IMD and is in wireless communication with external device 12, as illustrated in FIG. 1. In some examples, IMD 10 may be coupled to one or more leads. In some examples, IMD 10 may be implanted outside of a thoracic cavity of patient 4 (e.g., subcutaneously in the pectoral location illustrated in FIG. 1). IMD 10 may be positioned near the sternum near and/or just below the level of heart 6.

In some examples, IMD 10 may take the form of a Reveal LINQ™ Insertable Cardiac Monitor (ICM) or a Holter Heart Monitor, both available from Medtronic plc, of Dublin, Ireland. External device 12 may be a computing device configured for use in settings such as a home, clinic, or hospital, and may further be configured to communicate with IMD 10 via wireless telemetry. For example, external device 12 may be coupled to computing system 24 via network 25. Computing system 24 may include a remote patient monitoring system, such as Carelink®, available from Medtronic plc, of Dublin, Ireland. External device 12 may, in some examples, comprise a communication device such as a programmer, an external monitor, or a mobile device, such as a mobile phone, a "smart" phone, a laptop, a tablet computer, a personal digital assistant (PDA), etc.

In some examples, the example techniques and systems described herein may be used with an external medical device in addition to, or instead of IMD 10. In some examples, the external medical device is a wearable electronic device, such as the SEEQ™ Mobile Cardiac Telemetry (MCT) system available from Medtronic plc, of Dublin, Ireland, or another type of wearable "smart" electronic apparel, such as a "smart" watch, "smart" patch, or "smart" glasses. Such an external medical device may be positioned externally to patient 4 (e.g., positioned on the skin of patient 4) and may carry out any or all of the functions described herein with respect to IMD 10.

In some examples, a user, such as a physician, technician, surgeon, electro-physiologist, or other clinician, may interact with external device 12 to retrieve physiological or diagnostic information from IMD 10. In some examples, a user, such as patient 4 or a clinician as described above, may also interact with external device 12 to program IMD 10, e.g., select or adjust values for operational parameters of IMD 10. In some examples, external device 12 acts as an access point to facilitate communication with IMD 10 via network 25, e.g., by computing system 24. Computing system 24 may comprise computing devices configured to allow a user to interact with IMD 10 via network 25

In some examples, computing system 24 includes at least one of a handheld computing device, computer workstation, server or other networked computing device, smartphone, tablet, or external programmer that includes a user interface for presenting information to and receiving input from a user. In some examples, computing system 24 may include one or more devices that implement a machine learning system 150, such as neural network, a deep learning system, or other type of predictive analytics system. A user, such as a physician, technician, surgeon, electro-physiologist, or other clinician, may interact with computing system 24 to retrieve physiological or diagnostic information from IMD 10. A user may also interact with computing system 24 to program IMD 10, e.g., select values for operational parameters of the IMD. Computing system 24 may include a processor configured to evaluate EGM and/or other sensed signals transmitted from IMD 10 to computing system 24.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers, and may thus form part of a large-scale public network infrastructure, e.g., the Internet. Network 25 may provide computing devices, such as computing system 24 and IMD 10, access to the Internet, and may provide a communication framework that allows the computing devices to communicate with one another. In some examples, network 25 may be a private network that provides a communication framework that allows computing system 24, IMD 10, and/or external device 12 to communicate with one another but isolates one or more of computing system 24, IMD 10, or external device 12 from devices external to network 25 for security purposes. In some examples, the communications between computing system 24, IMD 10, and external device 12 are encrypted.

External device 12 and computing system 24 may communicate via wireless communication over network 25 using any techniques known in the art. In some examples, computing system 24 is a remote device that communicates with external device 12 via an intermediary device located in network 25, such as a local access point, wireless router, or gateway. While in the example of FIG. 1, external device 12 and computing system 24 communicate over network 25, in some examples, external device 12 and computing system 24 communicate with one another directly. Examples of communication techniques may include, for example, communication according to the Bluetooth® or BLE protocols. Other communication techniques are also contemplated. Computing system 24 may also communicate with one or more other external devices using a number of known communication techniques, both wired and wireless.

In any such examples, processing circuitry of medical device system 2 may transmit patient data, including cardiac electrogram data, for patient 4 to a remote computer (e.g., external device 12). In some examples, processing circuitry of medical device system 2 may transmit a determination that patient 4 is undergoing an episode of cardiac arrhythmia such as an episode of bradycardia, tachycardia, atrial fibrillation, ventricular fibrillation, or AV Block.

External device 12 may be a computing device (e.g., used in a home, ambulatory, clinic, or hospital setting) to communicate with IMD 10 via wireless telemetry. External device 12 may include or be coupled to a remote patient monitoring system, such as Carelink®, available from Medtronic plc, of Dublin, Ireland. In some examples, external device 12 may receive data, alerts, patient physiological information, or other information from IMD 10.

External device 12 may be used to program commands or operating parameters into IMD 10 for controlling its functioning (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule and/or may occur in response to a remote or local user command. Programmers, external monitors, and consumer devices are examples of external devices 12 that may be used to interrogate IMD 10. Examples of communication techniques used by IMD 10 and external device 12 include radiofrequency (RF) telemetry, which may be an RF link established via Bluetooth, WiFi, or medical implant communication service (MICS). In some examples, external device 12 may include a user interface configured to allow patient 4, a clinician, or another user to remotely interact with IMD 10. In some such examples, external device 12, and/or any other device of medical device system 2, may be a wearable device, (e.g., in the form of a watch, necklace, or other wearable item).

Medical device system 2 is an example of a medical device system configured to perform cardiac arrhythmia detection, verification, and reporting. In accordance with the techniques of the disclosure, medical device system 2 implements machine learning arrhythmia detection to detect and classify cardiac arrhythmias in patient 4. Additional examples of the one or more other implanted or external devices may include an implanted, multi-channel cardiac pacemaker, ICD, IPG, leadless (e.g., intracardiac) pacemaker, extravascular pacemaker and/or ICD, or other IMD or combination of such IMDs configured to deliver CRT to heart 6, an external monitor, an external therapy delivery device such as an external pacing or electrical stimulation device, or a drug pump.

Communication circuitry of each of the devices of medical device system 2 (e.g., IMD 10 and external device 12) may enable the devices to communicate with one another. In addition, although one or more sensors (e.g., electrodes) are described herein as being positioned on a housing of IMD 10, in other examples, such sensors may be positioned on a housing of another device implanted in or external to patient 4. In such examples, one or more of the other devices may include processing circuitry configured to receive signals from the electrodes or other sensors on the respective devices and/or communication circuitry configured to transmit the signals from the electrodes or other sensors to another device (e.g., external device 12) or server.

In accordance with the techniques of the disclosure, medical device system 2 explains and visualizes an output of machine learning system 150 that detects cardiac arrhythmia in a patient. Machine learning system 150 may provide tools for detecting and classifying episodes of arrhythmia in patient 4. However, the foundations for the conclusions drawn by machine learning system 150 may be difficult to convey. As discussed in more detail below, medical device system 2 functions to simplify the conclusions drawn by machine learning system 150 with respect to the detection of cardiac arrhythmia in patient 4. Further, medical device system 2 presents such information in a manner that is comprehensible to users of differing ability, including subject matter experts and non-experts alike.

In one example, computing system 24 receives cardiac electrogram data sensed by a medical device, such as one of IMD 10 and external device 12. Computing system 24 applies a machine learning model of machine learning system 150, trained using cardiac electrogram data for a plurality of patients, to the received cardiac electrogram data to determine, based on the machine learning model, that an episode of arrhythmia has occurred in patient 4. Machine learning system 150 further determines a level of confidence in the determination that the episode of arrhythmia has occurred in patient 4. In response to determining that the level of confidence is greater than a predetermined threshold, computing system 24 displays, to a user, a portion of the cardiac electrogram data, an indication that the episode of arrhythmia has occurred, and an indication of the level of confidence that the episode of arrhythmia has occurred. In some examples, computing system 24 provides more detailed information to advanced users and less detailed information to basic users.

In another example, computing system 24 receives cardiac electrogram data sensed by, e.g., IMD 10, and a selection of an arrhythmia type from a user. Computing system 24 applies machine learning system 150 to the received cardiac electrogram data to determine, based on the machine learning model of machine learning system 150, that an episode of arrhythmia of the selected type has occurred in patient 4 and a level of confidence in the determination that the episode of arrhythmia of the selected type has occurred. Computing system 24 outputs, for display, at least a portion of the cardiac electrogram data, a first indication that the episode of arrhythmia of the selected type has occurred in patient 4, and a second indication of the level of confidence that the episode of arrhythmia of the selected type has occurred in patient 4.

The techniques of the disclosure may provide specific improvements to the field of machine learning systems that perform cardiac arrhythmia detection and classification. For example, the techniques disclosed herein may allow for more clear explainability and visualization of the analysis performed by machine learning system 150. Further, the techniques described herein may allow for quick and patient-specific interpretation of cardiac electrogram data for use by users of many different skill levels. The techniques disclosed herein may reduce the amount of training required by users to make use of conclusions provided by machine learning systems that perform cardiac arrhythmia detection and classification, as well as enable the use of such machine learning systems in a wider variety of systems. Accordingly, the techniques disclosed herein may enable more accurate and faster diagnosis and classification of cardiac arrhythmia in patients, while reducing the amount of expertise required by clinicians to diagnose and provide therapy for such cardiac arrhythmia.

Figure 2:
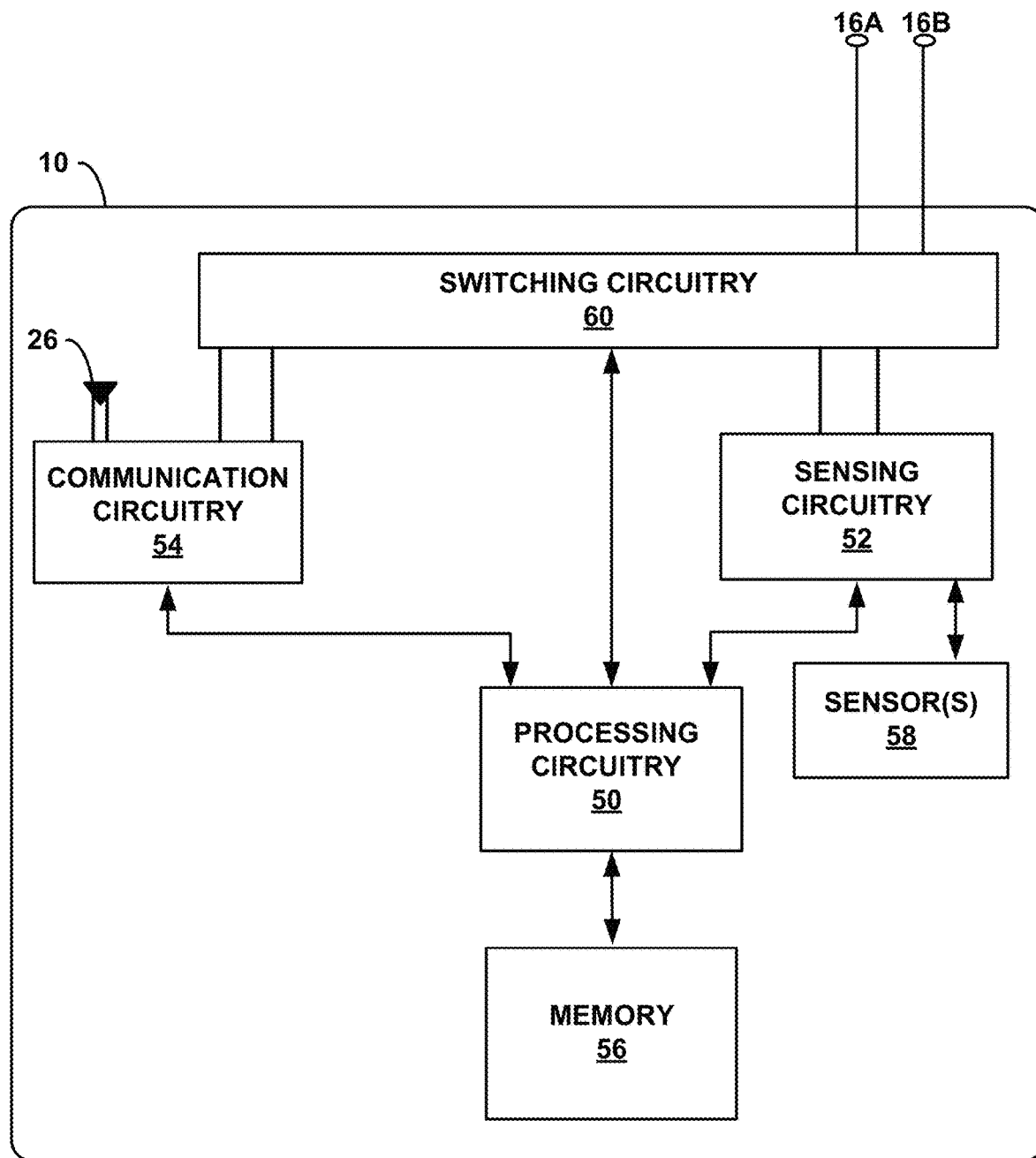
FIG. 2 is a block diagram illustrating an example of the implantable medical device of FIG. 1.

FIG. 2 is a block diagram illustrating an example of the leadless implantable medical device of FIG. 1. As shown in FIG. 2, IMD 10 includes processing circuitry 50 sensing circuitry 52, communication circuitry 54, memory 56, sensors 58, switching circuitry 60, and electrodes 16A, 16B (hereinafter "electrodes 16"), one or more of which may be disposed within a housing of IMD 10. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 and communication circuitry 54 may be selectively coupled to electrodes 16A, 16B via switching circuitry 60 as controlled by processing circuitry 50. Sensing circuitry 52 may monitor signals from electrodes 16A, 16B in order to monitor electrical activity of a heart of patient 4 of FIG. 1 and produce cardiac electrogram data for patient 4. Sensing circuitry 52 may produce a digitized version of the cardiac electrogram as well as indications of the timing of depolarizations. In some examples, processing circuitry 50 may perform feature delineation of the sensed cardiac electrogram data to detect an episode of cardiac arrhythmia of patient 4. In some examples, processing circuitry 50 transmits, via communication circuitry 54, the cardiac electrogram data for patient 4 to an external device, such as external device 12 of FIG. 1. For example, IMD 10 sends digitized cardiac electrogram data to network 25 for processing by machine learning system 150 of FIG. 1. In some examples, IMD 10 transmits one or more segments of the cardiac electrogram data in response to detecting, via feature delineation, an episode of arrhythmia. In another example, IMD 10 transmits one or more segments of the cardiac electrogram data in response to instructions from external device 12 (e.g., when patient 4 experiences one or more symptoms of arrhythmia and inputs a command to external device 12 instructing IMD 10 to upload the cardiac electrogram data for analysis by a monitoring center or clinician). The cardiac electrogram data may be processed by machine learning system 150 to detect and classify cardiac arrhythmia as described in detail below.

In some examples, IMD 10 includes one or more sensors 58, such as one or more accelerometers, microphones, and/or pressure sensors. Sensing circuitry 52 may monitor signals from sensors 58 and transmit patient data obtained from sensors 58, to an external device, such as external device 12 of FIG. 1, for analysis. In some examples, sensing circuitry 52 may include one or more filters and amplifiers for filtering and amplifying signals received from one or more of electrodes 16A, 16B and/or other sensors 58. In some examples, sensing circuitry 52 and/or processing circuitry 50 may include a rectifier, filter and/or amplifier, a sense amplifier, comparator, and/or analog-to-digital converter.

Communication circuitry 54 may include any suitable hardware, firmware, software or any combination thereof for communicating with another device, such as external device 12 or another medical device or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In some examples, communication circuitry 54 may communicate with external device 12. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device. In some examples, the clinician may select one or more parameters defining how IMD 10 senses cardiac electrogram data of patient 4.

One or more components of IMD 10 may be coupled to a power source (not depicted in FIG. 2), which may include a rechargeable or non-rechargeable battery positioned within a housing of IMD 10. A non-rechargeable battery may be selected to last for several years, while a rechargeable battery may be inductively charged from an external device, e.g., on a daily or weekly basis.

In some examples, processing circuitry 50 senses cardiac electrogram data of patient 4 via sensing circuitry 52 and uploads such cardiac electrogram data to external device 12 of FIG. 1. In some examples, processing circuitry 50 performs feature delineation of the sensed cardiac electrogram data to perform a preliminary detection of cardiac arrhythmia, and only uploads the cardiac electrogram data of patient 4 to external device 12 in response to detecting an episode of cardiac arrhythmia. In some examples, the feature delineation performed by IMD 10 is of a reduced complexity so as to conserve power in IMD 10.

As described herein, feature delineation refers to the use of features obtained through signal processing for use in detecting or classifying an episode cardiac arrhythmia. Typically, feature delineation involves the use of engineered rules to identify or extract features in cardiac electrogram data, measure characteristics of such features, and use the measurements to detect or classify arrhythmia. For example, feature delineation may be used to identify features such as R-waves, QRS complexes, P-waves, T-waves, rates of such features, intervals between such features, feature morphology, widths or amplitudes of such features, or other or other types of cardiac features or characteristics of such features not expressly described herein. Feature delineation may include feature extraction, signal filtering, peak detection, refractory analysis, or other types of signal processing, feature engineering, or detection rule development. Feature delineation algorithms may be optimized for real-time, embedded, and low-power applications, such as for use by an implantable medical device. However, feature delineation algorithms may require expert design and feature engineering to accurately detect arrhythmia in a patient.

In contrast to feature delineation techniques for cardiac arrhythmia detection and classification, machine learning techniques may be used for cardiac arrhythmia detection and classification. As described herein, machine learning refers the use of a machine learning model, such as a neural network or deep-learning model, that is trained on training datasets to detect cardiac arrhythmia from cardiac electrogram data. Machine learning techniques may be contrasted from feature delineation in that feature delineation relies on signal processing, which machine learning systems may "learn" underlying features present in cardiac electrogram data indicative of an episode of arrhythmia without requiring knowledge or understanding of the relationship between the features and the episode of arrhythmia on behalf of the system designer.

Although described herein in the context of example IMD 10 that senses cardiac electrogram data of patient 4, the techniques for cardiac arrhythmia detection disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a medical device external to patient 4, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses, a "smart" patch, or a "smart" watch.

Figure 3:
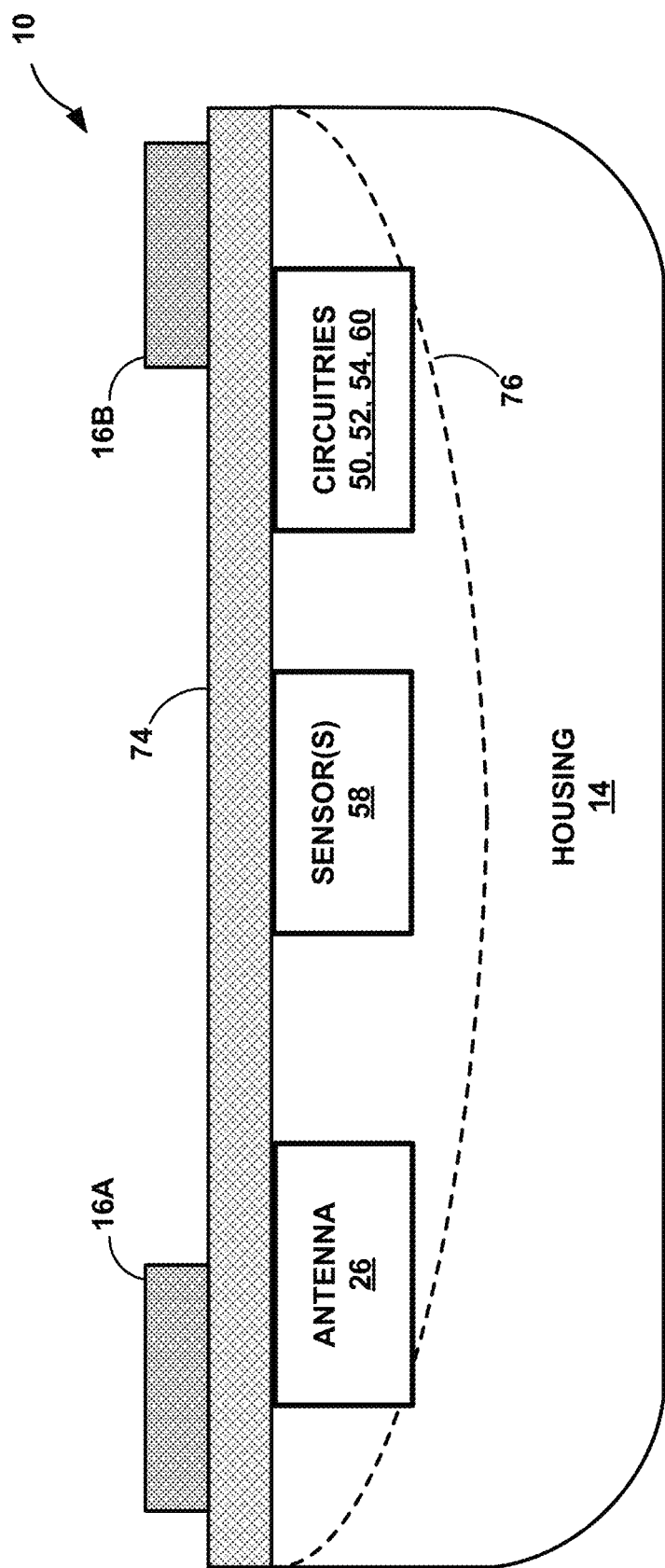
FIG. 3 is a block diagram illustrating another example of the implantable medical device of FIG. 1.

FIG. 3 is a block diagram illustrating another example of the leadless implantable medical device of FIG. 1. The components of FIG. 3 may not necessarily be drawn to scale, but instead may be enlarged to show detail. Specifically, FIG. 3 is a block diagram of a top view of an example configuration of an IMD 10 of FIG. 1.

FIG. 3 is a conceptual drawing illustrating an example IMD 10 that may include components substantially similar to IMD 10 of FIG. 1. In addition to the components illustrated in FIGS. 1 and 2, the example of IMD 10 illustrated in FIG. 3 also may include a wafer-scale insulative cover 74, which may help insulate electrical signals passing between electrodes 16A, 16B on housing 14 and processing circuitry 50. In some examples, insulative cover 74 may be positioned over an open housing 14 to form the housing for the components of IMD 10B. One or more components of IMD 10B (e.g., antenna 26, processing circuitry 50, sensing circuitry 52, communication circuitry 54, and/or switching circuitry 60 may be formed on a bottom side of insulative cover 74, such as by using flip-chip technology. Insulative cover 74 may be flipped onto housing 14. When flipped and placed onto housing 14, the components of IMD 10B formed on the bottom side of insulative cover 74 may be positioned in a gap 76 defined by housing 14. Housing 14 may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

In some examples, IMD 10 collects, via sensing circuitry 52 and/or sensors 58, patient data of patient 4 including cardiac electrogram data. Sensors 58 may include one or more sensors, such as one or more accelerometers, pressure sensors, optical sensors for 02 saturation, etc. In some examples, the patient data includes one or more of an activity level of the patient, a heartrate of the patient, a posture of the patient, a cardiac electrogram of the patient, a blood pressure of the patient, accelerometer data for the patient, or other types of patient parametric data. IMD 10 uploads, via communication circuitry 54, the patient data to external device 12, which may in turn upload such data to computing system 24 over network 25. In some examples, IMD 10 uploads the patient data to computing system 24 on a daily basis. In some examples, the patient data includes one or more values that represent average measurements of patient 4 over a long-term time period (e.g., about 24 hours to about 48 hours). In this example, IMD 10 both uploads the patient data to computing system 24 and performs short-term monitoring of patient 4 (as described below). However, in other examples, the medical device that processes the patient data to detect and/or classify arrhythmia in patient 4 is different from the medical device that performs short-term monitoring of patient 4.

Figure 4:
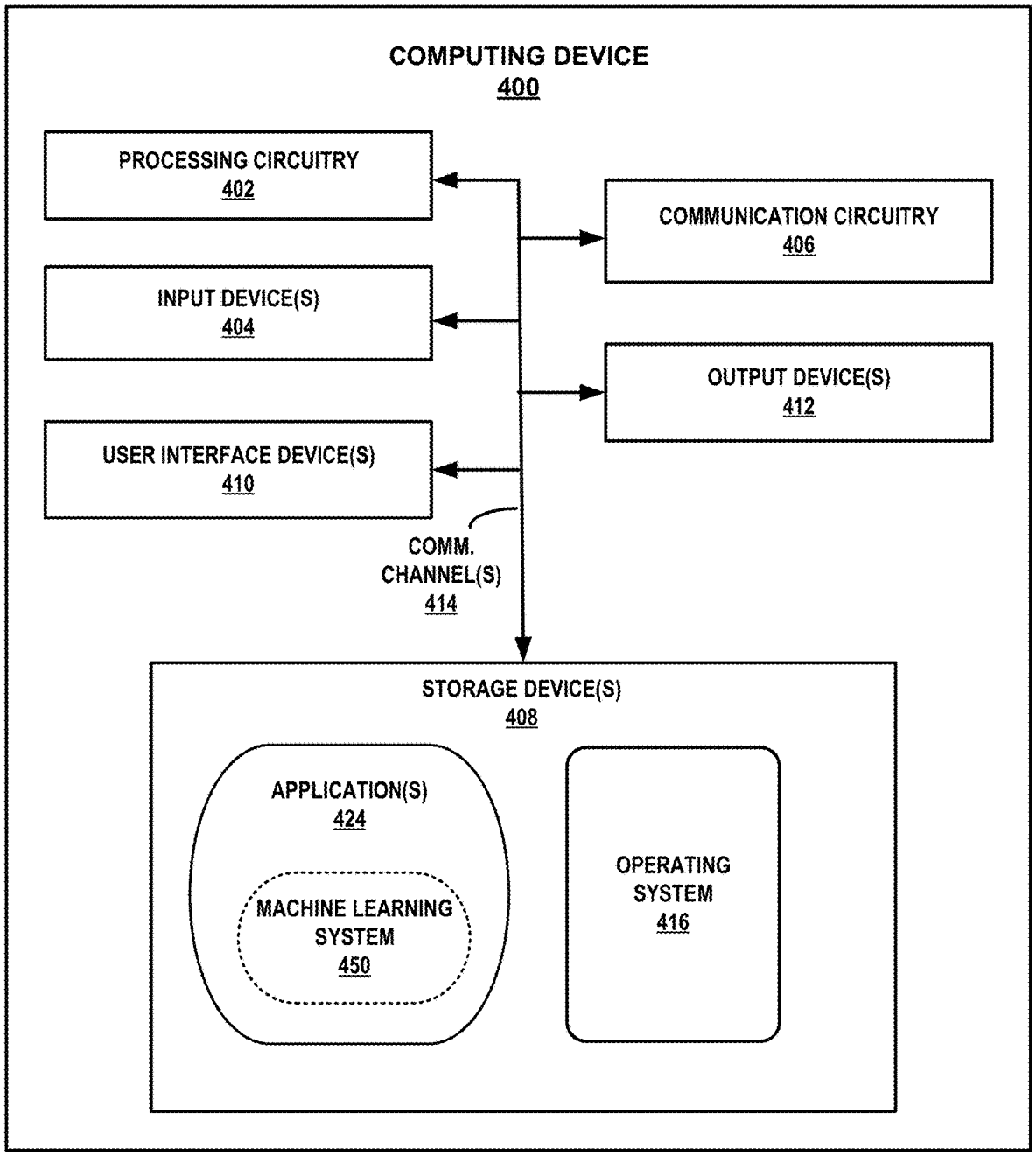
FIG. 4 is a block diagram illustrating an example computing device that operates in accordance with one or more techniques of the present disclosure.

FIG. 4 is a block diagram illustrating an example computing device 400 that operates in accordance with one or more techniques of the present disclosure. In one example, computing device 400 is an example implementation of computing system 24 of FIG. 1. In one example, computing device 400 includes processing circuitry 402 for executing applications 424 that include machine learning system 450 or any other applications described herein. Although shown in FIG. 4 as a stand-alone computing device 400 for purposes of example, computing device 400 may be any component or system that includes processing circuitry or other suitable computing environment for executing software instructions and, for example, need not necessarily include one or more elements shown in FIG. 4 (e.g., input devices 404, communication circuitry 406, user interface devices 410, or output devices 412; and in some examples components such as storage device(s) 408 may not be co-located or in the same chassis as other components). In some examples, computing device 400 may be a cloud computing system distributed across a plurality of devices.

As shown in the example of FIG. 4, computing device 400 includes processing circuitry 402, one or more input devices 404, communication circuitry 406, one or more storage devices 408, user interface (UI) device(s) 410, and one or more output devices 412. Computing device 400, in one example, further includes one or more application(s) 424 such as machine learning system 450, and operating system 416 that are executable by computing device 400. Each of components 402, 404, 406, 408, 410, and 412 are coupled (physically, communicatively, and/or operatively) for inter-component communications. In some examples, communication channels 414 may include a system bus, a network connection, an inter-process communication data structure, or any other method for communicating data. As one example, components 402, 404, 406, 408, 410, and 412 may be coupled by one or more communication channels 414.

Processing circuitry 402, in one example, is configured to implement functionality and/or process instructions for execution within computing device 400. For example, processing circuitry 402 may be capable of processing instructions stored in storage device 408. Examples of processing circuitry 402 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 408 may be configured to store information within computing device 400 during operation. Storage device 408, in some examples, is described as a computer-readable storage medium. In some examples, storage device 408 is a temporary memory, meaning that a primary purpose of storage device 408 is not long-term storage. Storage device 408, in some examples, is described as a volatile memory, meaning that storage device 408 does not maintain stored contents when the computer is turned off. Examples of volatile memories include random access memories (RAM), dynamic random access memories (DRAM), static random access memories (SRAM), and other forms of volatile memories known in the art. In some examples, storage device 408 is used to store program instructions for execution by processing circuitry 402. Storage device 408, in one example, is used by software or applications 424 running on computing device 400 to temporarily store information during program execution.

Storage devices 408, in some examples, also include one or more computer-readable storage media. Storage devices 408 may be configured to store larger amounts of information than volatile memory. Storage devices 408 may further be configured for long-term storage of information. In some examples, storage devices 408 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 400, in some examples, also includes communication circuitry 406. Computing device 400, in one example, utilizes communication circuitry 406 to communicate with external devices, such as IMD 10 and external device 12 of FIG. 1. Communication circuitry 406 may include a network interface card, such as an Ethernet card, an optical transceiver, a radio frequency transceiver, or any other type of device that can send and receive information. Other examples of such network interfaces may include 3G and WiFi radios.

Computing device 400, in one example, also includes one or more user interface devices 410. User interface devices 410, in some examples, are configured to receive input from a user through tactile, audio, or video feedback. Examples of user interface devices(s) 410 include a presence-sensitive display, a mouse, a keyboard, a voice responsive system, video camera, microphone or any other type of device for detecting a command from a user. In some examples, a presence-sensitive display includes a touch-sensitive screen.

One or more output devices 412 may also be included in computing device 400. Output device 412, in some examples, is configured to provide output to a user using tactile, audio, or video stimuli. Output device 412, in one example, includes a presence-sensitive display, a sound card, a video graphics adapter card, or any other type of device for converting a signal into an appropriate form understandable to humans or machines. Additional examples of output devices 412 include a speaker, a cathode ray tube (CRT) monitor, a liquid crystal display (LCD), or any other type of device that can generate intelligible output to a user.

Computing device 400 may include operating system 416. Operating system 416, in some examples, controls the operation of components of computing device 400. For example, operating system 416, in one example, facilitates the communication of one or more applications 424 and long-term prediction module 450 with processing circuitry 402, communication circuitry 406, storage device 408, input device 404, user interface devices 410, and output device 412.

Application(s) 422 may also include program instructions and/or data that are executable by computing device 400. Example application(s) 422 executable by computing device 400 may include machine learning system 450. Other additional applications not shown may alternatively or additionally be included to provide other functionality described herein and are not depicted for the sake of simplicity.

In accordance with the techniques of the disclosure, computing device 400 applies a machine learning model of machine learning system 450 to patient data sensed by IMD 10 to detect and classify an episode of arrhythmia occurring in patient 10. In some examples, machine learning system 450 is an example of machine learning system 150 of FIG. 1.

In some examples, the machine learning model implemented by machine learning system 450 is trained with training data that comprises cardiac electrogram data for a plurality of patients labeled with descriptive metadata. For example, during a training phase, machine learning system 450 processes a plurality of ECG waveforms. Typically, the plurality of ECG waveforms are from a plurality of different patients. Each ECG waveform is labeled with one or more episodes of arrhythmia of one or more types. For example, a training ECG waveform may include a plurality of segments, each segment labeled with a descriptor that specifies an absence of arrhythmia or a presence of an arrhythmia of a particular classification (e.g., bradycardia, tachycardia, atrial fibrillation, ventricular fibrillation, or AV Block). In some examples, a clinician labels the presence of arrhythmia in each ECG waveform by hand. In some examples, the presence of arrhythmia in each ECG waveform is labeled according to classification by a feature delineation algorithm. Machine learning system 450 may operate to convert the training data into vectors and tensors (e.g., multi-dimensional arrays) upon which machine learning system 450 may apply mathematical operations, such as linear algebraic, nonlinear, or alternative computation operations. Machine learning system 450 uses the training data 104 to teach the machine learning model to weigh different features depicted in the cardiac electrogram data. In some examples, machine learning system 450 uses the cardiac electrogram data to teach the machine learning model to apply different coefficients that represent one or more features in a cardiac electrogram as having more or less importance with respect to an occurrence of a cardiac arrhythmia of a particular classification. By processing numerous such ECG waveforms labeled with episodes of arrhythmia, machine learning system 450 may build and train a machine learning model to receive cardiac electrogram data from a patient, such as patient 4 of FIG. 1, that machine learning system 450 has not previously analyzed, and process such cardiac electrogram data to detect the presence or absence of arrhythmia of different classifications in the patient with a high degree of accuracy. Typically, the greater the amount of cardiac electrogram data on which machine learning system 450 is trained, the higher the accuracy of the machine learning model in detecting or classifying cardiac arrhythmia in new cardiac electrogram data.

After machine learning system 450 has trained the machine learning model, machine learning system 450 may receive patient data, such as cardiac electrogram data, for a particular patient, such as patient 4. Machine learning system 450 applies the trained machine learning model to the patient data to detect an occurrence of an episode of cardiac arrhythmia in patient 4. Further, machine learning system 450 applies the trained machine learning model to the patient data to classify the episode of cardiac arrhythmia in patient as indicative of a particular type of arrhythmia. In some examples, machine learning system 450 may output a determination that the episode of cardiac arrhythmia is indicative of a particular type of arrhythmia, as well as a level of confidence in the determination. In response to determining that the level of confidence in the determination is greater than a predetermined threshold (e.g., 50%, 75%, 90%, 95%, 99%), computing device 400 may classify that the episode of cardiac arrhythmia as the particular type of arrhythmia and output, for display to a user, at least a portion of the cardiac electrogram data (e.g., a portion of an ECG during which the episode of arrhythmia occurred), a first indication that the episode of arrhythmia has occurred in patient 4, and a second indication of the level of confidence in the determination that the episode of arrhythmia has occurred.

In some examples, machine learning system 150 may process one or more cardiac features of cardiac electrogram data instead of the raw cardiac electrogram data itself. The one or more cardiac features may be obtained via feature delineation performed by IMD 10, as described above. The cardiac features may include, e.g., one or more of a mean heartrate of the patient, a minimum heartrate of the patient, a maximum heartrate of the patient, a PR interval of a heart of the patient, a variability of heartrate of the patient, one or more amplitudes of one or more features of an electrocardiogram (ECG) of the patient, or an interval between the or more features of the ECG of the patient, a T-wave alternans, QRS morphology measures, or other types of cardiac features not expressly described herein. In such example implementations, machine learning system may train the machine learning model via a plurality of training cardiac features labeled with episodes of arrhythmia, instead of the plurality of ECG waveforms labeled with episodes of arrhythmia as described above.

In some examples, machine learning system 450 may process the cardiac electrogram data to derive a classification of the episode of arrhythmia (e.g., bradycardia, tachycardia, atrial fibrillation, ventricular fibrillation, or AV Block). Further, machine learning system 450 may determine, for each of arrhythmia type classification, class activation data indicating varying likelihoods of the classification over the period of time. For a given arrhythmia type, an amplitude of such likelihood values at different times corresponds to a probability that an arrhythmia is occurring at that time, with higher values corresponding to higher probability.

Computing device 400 may use class activation mapping to identify regions of an input time series, e.g., of cardiac EGM data, that constitute the reason for the time series being given a particular classification by the machine learning model of machine learning system 450. A class activation map for a given classification may be a univariate time series where each element (e.g., at each timestamp at the sampling frequency of the input time series) may be a weighted sum or other value derived from the outputs of an intermediate layer of a neural network or other machine learning model. The intermediate layer may be a global average pooling layer and/or last layer prior to the output layer neurons for each classification In some examples, machine learning system 450 may apply the machine learning model to other types of data to determine that an episode of arrhythmia has occurred in patient 4. For example, machine learning system 450 may apply the machine learning model to one or more characteristics of cardiac electrogram data that are correlated to arrhythmia in the patient, an activity level of IMD 10, an input impedance of IMD 10, or a battery level of IMD 10.

In further examples, processing circuitry 402 may generate, from the cardiac electrogram data, an intermediate representation of the cardiac electrogram data. For example, processing circuitry 402 may apply one or more signal processing, signal decomposition, wavelet decomposition, filtering, or noise reduction operations to the cardiac electrogram data to generate the intermediate representation of the cardiac electrogram data. In this example, machine learning system 450 processes such an intermediate representation of the cardiac electrogram data to detect and classify an episode of arrhythmia in patient 4. Furthermore, machine learning system may train the machine learning model via a plurality of training intermediate representations labeled with episodes of arrhythmia, instead of the plurality of raw ECG waveforms labeled with episodes of arrhythmia as described above. The use of such intermediate representations of the cardiac electrogram data may allow for the training and development of a lighter-weight, less computationally complex machine learning model by machine learning system 450. Further, the use of such intermediate representations of the cardiac electrogram data may require less iterations and fewer training data to build an accurate machine learning model, as opposed to the use of raw cardiac electrogram data to train the machine learning model.

In some examples, computing system 24 may use machine learning system 150 to detect other types of arrhythmias beyond the ones in detected in the feature delineation screening analysis. For example, arrhythmia detection algorithms for performing feature delineation implemented by low-power devices such as IMD 10 may not be designed to detect less-frequently occurring arrhythmias, such as AV Blocks. Machine learning system 150 may train a machine learning model on large datasets where such arrhythmias are available, thereby providing finer granularity and higher accuracy over feature delineation performed by, e.g., IMD 10 alone. Therefore, the use of machine learning system 150 may expand the arrhythmia diagnosis capability of system 2 by allowing IMD 10 to implement a generic screening algorithm using feature delineation followed by the use of machine learning system 150 that implements a machine learning model that can provide a wider range of arrhythmia detection. After detecting a type of arrhythmia that was not detected by feature delineation, computing system 24 may nevertheless use feature delineation, such as QRS detection, to assist in characterizing and reporting the other types of arrhythmias detected by the machine learning model of machine learning system 150.

In some examples, computing system 24 may tailor machine learning system 150 to the specific use case. For example, machine learning system 150 may implement a machine learning model specific to detecting AV Blocks and bradycardia where patient 4 is a post-TAVR patient. As another example, machine learning system 150 may implement a machine learning model specific to detecting PVCs such that PVC burden may be used to risk-stratify patients who might be indicated for ICDs.

Figure 5:
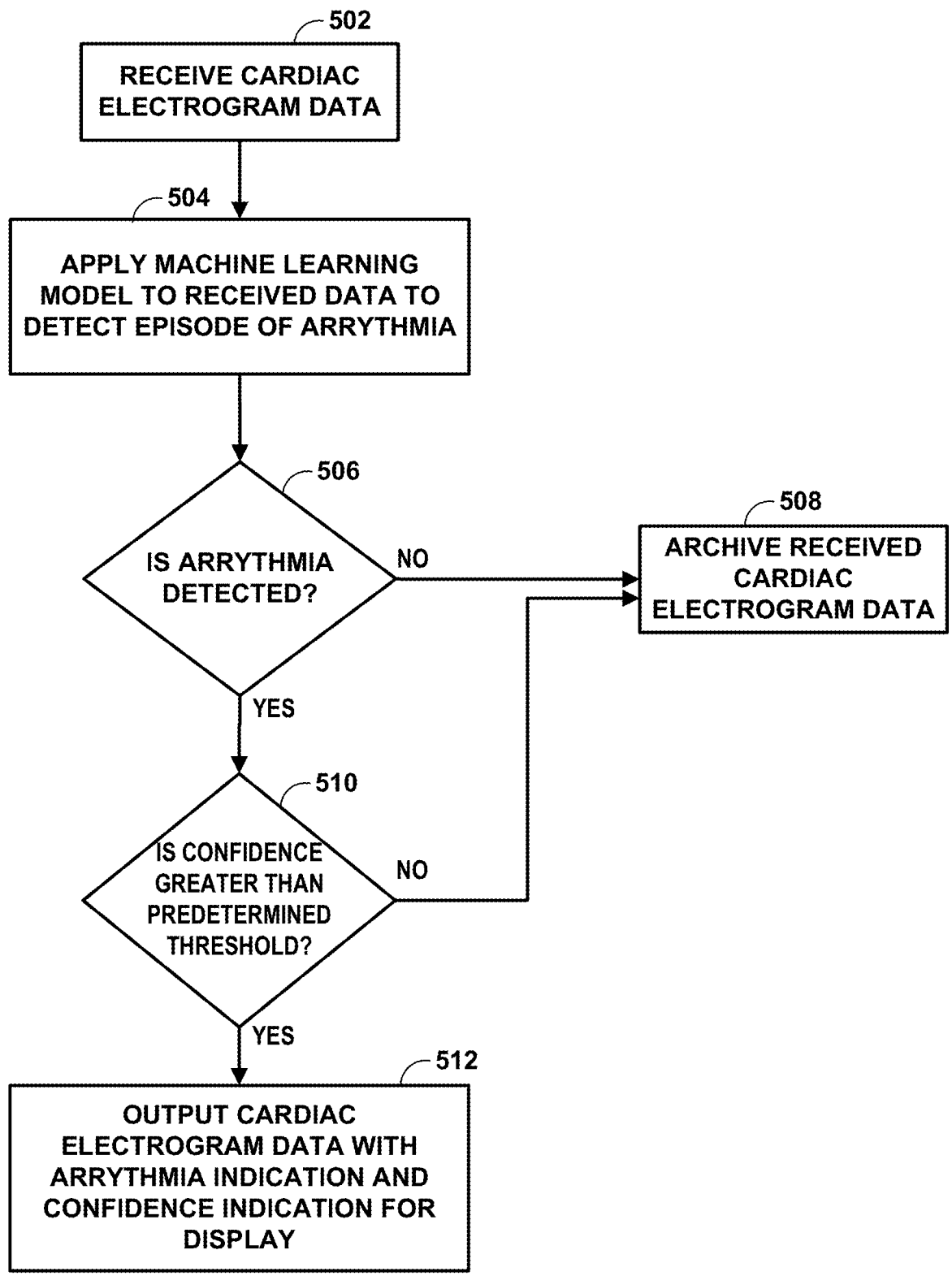
FIG. 5 is a flowchart illustrating an example operation in accordance with the techniques of the disclosure.

FIG. 5 is a flowchart illustrating an example operation in accordance with the techniques of the disclosure. For convenience, FIG. 5 is described with respect to FIG. 1. In some examples, the operation of FIG. 5 is an operation for explaining and visualizing an output of machine learning system 150 that detects an episode of cardiac arrhythmia in patient 4.

As depicted in FIG. 5, IMD 10 senses cardiac electrogram data of patient 4. The cardiac electrogram data can be, e.g., an episodic ECG of patient 4 or a full-disclosure ECG of patient 4. Further, the cardiac electrogram data of patient 4 may be from a single-channel or multi-channel system. For simplicity, in the example of FIG. 5, the cardiac electrogram data of patient 4 is described as single-channel episodic ECG data. IMD 10 uploads the cardiac electrogram data to external device 12. Computing system 24 receives the cardiac electrogram data from external device 12 (502).

Machine learning system 150 of computing system 24 applies a machine learning model to the received cardiac electrogram data to detect an episode of arrhythmia in patient 4 (504). In some examples, the machine learning model is trained with a plurality of ECG episodes annotated by a clinician or a monitoring center for arrhythmias of several different types. In one example, machine learning system 150 applies the machine learning model to one or several subsegments of a normalized input ECG signal and generates arrhythmia labels and a likelihood of an occurrence of the arrhythmia. In some examples, machine learning system 150 determines that an episode of arrhythmia has occurred in patient 4 and determines a level of confidence in the determination that the episode of arrhythmia has occurred in patient 4. In some examples, machine learning system 150 determines whether an episode of arrhythmia of a plurality of different arrhythmia types has occurred in patient 4, as well as a level of confidence that an episode of arrhythmia of each arrhythmia type has occurred.

Computing system 24 determines whether machine learning system 150 has detected an episode of arrhythmia (506). In response to determining that machine learning system 150 has detected an episode of arrhythmia (e.g., "YES" block of 506), computing system 24 determines whether level of confidence in the determination is greater than a predetermined threshold (510). In some examples, the predetermined threshold is, e.g., 25%, 50%, 75%, 90%, 95%, 99%, etc. in some examples, computing system 24 determines whether the level of confidence in the determination is greater than a first predetermined threshold (e.g., 50%) and whether the level of confidence in the determination is greater than a second predetermined threshold (e.g., 90%). The first predetermined threshold may be associated with a medium level of confidence by machine learning system 150 that the episode of arrhythmia has occurred, while the second predetermined threshold may be associated with a high level of confidence by machine learning system 150.

In response to determining that the level of confidence is greater than the predetermined threshold (e.g., "YES" block of 510), computing system 24 outputs the cardiac electrogram data for review by a clinician. In some examples, computing system 24 outputs a portion of the cardiac electrogram data, a first indication that the episode of arrhythmia has occurred in patient 4, and a second indication of the level of certainty in the determination that the episode of arrhythmia has occurred in patient 4 (512). In some examples, computing system 24 selects a visualization method according to the level of confidence by machine learning system 150 that the episode of arrhythmia has occurred. For example, computing system 24 may apply color coding to indicate results (e.g., "green" for low confidence than an episode of arrhythmia has occurred, "yellow" for medium confidence than an episode of arrhythmia has occurred, or "red" for a high confidence than an episode of arrhythmia has occurred).

In some examples, computing system 24 uses different visualization techniques to indicate a type of arrhythmia. In some examples, computing system 24 presents an ECG waveform and an annotation to the waveform to indicate where the episode of arrhythmia has occurred. In some examples, the annotation includes highlighting a section of the ECG, indicating a start and/or stop time of the episode of arrhythmia, or applying a graphical icon or text to the section of the ECG. Computing system 24 may use a wide variety of different visualization techniques, such as color-coding, hatching, images or icons, shapes, indicators of different size, light, sound, textual notifications, etc. to simply the information conveyed to the user.

In one example, computing system 24 displays an indication that the episode of arrhythmia has occurred in the patient and one or more of the cardiac features that coincide with the episode of arrhythmia. In some examples, computing system 24 displays a classification of the episode of arrhythmia as a particular type of arrhythmia.

In some examples, computing system 24 displays a subsection of the cardiac electrogram data obtained from patient 4 that coincides with the episode of arrhythmia. For example, computing system 24 may identify a subsection of the cardiac electrogram data of patient 4, wherein the subsection comprises cardiac electrogram data for a first time period prior to the episode of arrhythmia (e.g., typically less than 10 minutes prior to the onset of the episode of arrhythmia), a second time period during the occurrence of the episode of arrhythmia, and a third time period after the episode of arrhythmia (e.g., typically less than 10 minutes after the cessation of the episode of arrhythmia).

As an example, a subsection of the cardiac electrogram data of patient 4 may be about 6 seconds in length and includes representative segments before, during, and after an episode of arrhythmia (if present in the cardiac electrogram data or waveform that is analyzed). In some examples, the episode duration differs by device type, and may further depend on a use case for the medical device, one or more settings of the medical device, or a particular type of arrhythmia sensed. For example, some types of arrhythmia self-terminate quickly, (resulting in a short duration episode), while other types of arrhythmia are sustained and of a length such that the recorded duration of the episode may depend on a designated memory space on the medical device. As an example, for atrial fibrillation (AF), the subsection of the cardiac electrogram data of patient 4 may include cardiac electrogram data during an onset time period, a segment of maximum AF likelihood, a segment of fastest AF rate, and an AF offset. Typically, a length of time of the cardiac electrogram data of the patient is greater than the first, second, and third time periods. Further, computing system 24 identifies one or more of the cardiac features that coincide with the first, second, and third time periods. computing system 24 displays the subsection of the cardiac electrogram data and the one or more of the cardiac features that coincide with the first, second, and third time periods.

In response to determining that machine learning system 150 has not detected an episode of arrhythmia (e.g., "NO" block of 506), or in response to determining that the level of confidence is not greater than the predetermined threshold (e.g., "NO" block of 510), computing system 24 archives the sensed cardiac electrogram data for review by a monitoring center or clinician at a later time (508).

Figure 6:
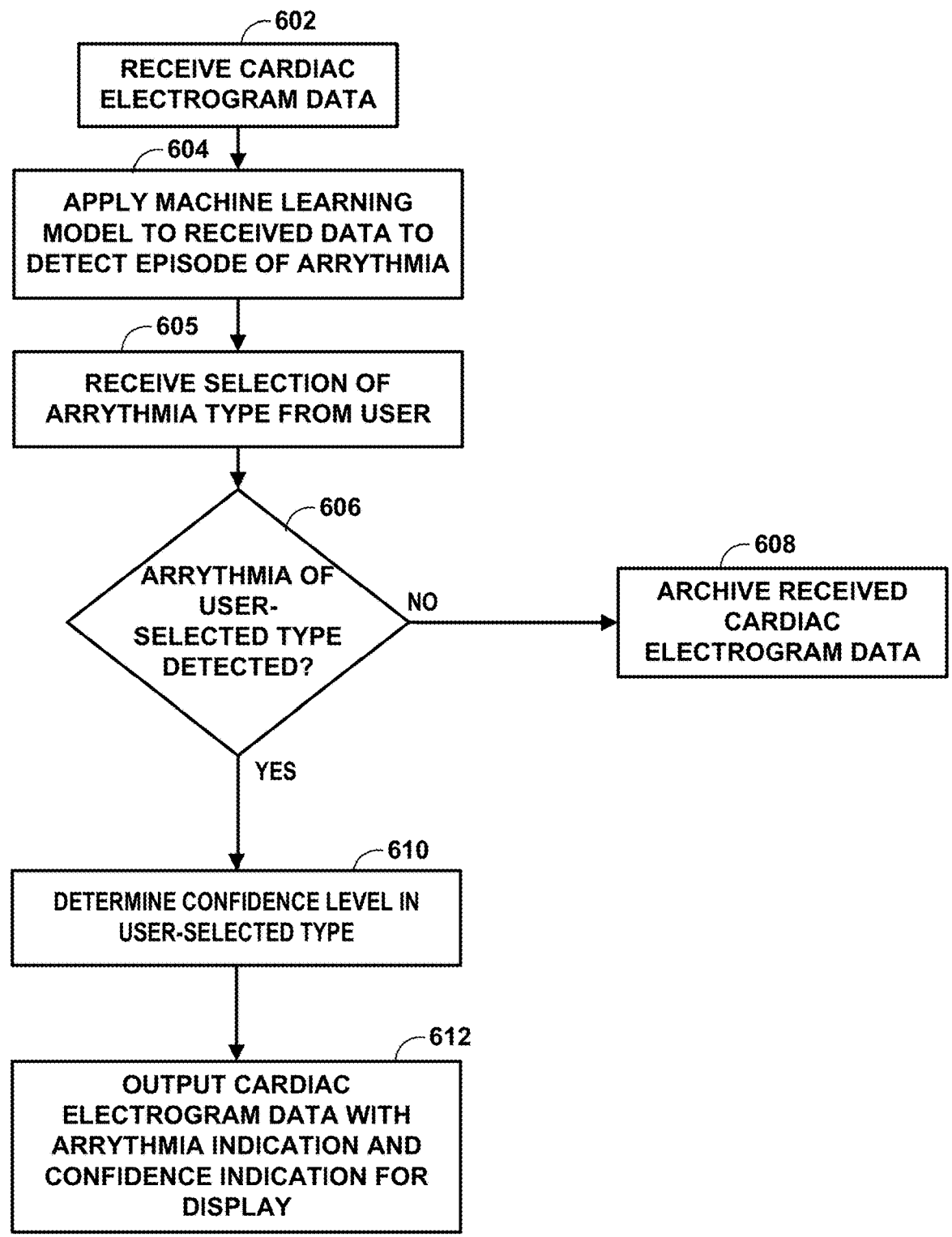
FIG. 6 is a flowchart illustrating an example operation in accordance with the techniques of the disclosure.

FIG. 6 is a flowchart illustrating an example operation in accordance with the techniques of the disclosure. For convenience, FIG. 6 is described with respect to FIG. 1. In some examples, the operation of FIG. 6 is an operation for explaining and visualizing an output of machine learning system 150 that detects an episode of cardiac arrhythmia of a type selected by a user.

The operation of FIG. 6 may be similar to the operation of FIG. 5 in that computing system 24 presents a visualization, such as a color-coded diagram, of detected arrhythmias and a corresponding confidence level that each arrhythmia is present. However, the operation of FIG. 6 allows a user to pre-select an arrhythmia of a specific type or classification. In response, computing system 24 filters the output to depict the likelihood of the presence of only the selected type(s) of arrhythmia on a location within the cardiac electrogram data, as well as a corresponding confidence level in the detection.

Computing system 24 receives the cardiac electrogram data from external device 12 (602). Machine learning system 150 of computing system 24 applies a machine learning model to the received cardiac electrogram data to detect an episode of arrhythmia in patient 4 (604). The operation of steps 602 and 604 may occur in a substantially similar fashion as steps 502 and 504 of FIG. 5, respectively.

Computing system 24 receives, from a user, a selection of a type of arrhythmia (605) for the specific patient. For example, computing system may receive, as an input from a user via an interface of computing system 24, a selection of an arrhythmia such as bradycardia, tachycardia, atrial fibrillation, ventricular fibrillation, or AV Block. Computing system 24 determines whether machine learning system 150 detects an episode of arrhythmia of the selected type (606) in the current and subsequent episodes from the specific patient. For example, in response to determining that machine learning system 150 has detected no episodes of arrhythmia of the selected type (e.g., "NO" block of 606), computing system 24 archives the sensed cardiac electrogram data for review by a monitoring center or clinician at a later time (608).

In response to determining that machine learning system 150 has detected at least one episode of arrhythmia of the selected type (e.g., "YES" block of 606), computing system 24 determines a level of confidence by machine learning system 150 that the episode of arrhythmia of the selected type has occurred in patient 4 (610). Furthermore, computing system 24 outputs a portion of the cardiac electrogram data, a first indication that the episode of arrhythmia has occurred in patient 4, and a second indication of the level of certainty in the determination that the episode of arrhythmia has occurred in patient 4 (612).

Accordingly, the operation of FIG. 6 allows a user to select a specific arrhythmia of interest. Computing system 24 may update the visual presentation based upon the user selection. Because computing system 24 updates its user interface based upon user input, in addition to displaying any arrhythmias detected with high and medium confidence levels, computing system 24 may also present potential episodes of arrhythmias that have been detected with a low confidence. In some examples where an arrhythmia is detected with a low confidence in the detection, an indicator that the determination is of the low confidence is prominently noted together with the corresponding value of the low confidence level in the detected arrhythmias. Thus, computing system 24 may present a visualization or explanation of arrhythmias of many different types (and certainties). Accordingly, a clinician may use computing system 24 to confirm a classification by the clinician of an arrhythmia of a particular type. This may increase the accuracy in diagnosis of patient 4 by a clinician, particularly for arrhythmias of types that are less prevalent and more difficult for clinicians to identify. Computing system 24 may further help identify subsequent occurrences of episodes of arrhythmia of previously-identified types.

In another example, computing system 24 receives, from a user, a classification of an episode of arrhythmia as being of a particular type of arrhythmia. Machine learning system 150 uses the received classification to train or update the machine learning model or the arrhythmia threshold to increase the accuracy and performance of machine learning model 150. This may allow for increasing the accuracy and performance of machine learning system 150 in detecting and classifying episodes of arrhythmias of types that are difficult to detect, episodes of arrhythmias of types that are dependent on a unique medical diagnosis particular to a particular patient, or episodes of arrhythmias of types for which data is scarce, uncommon, or of low prevalence, or of arrhythmias whose detection performance in a specific patient might be sub-optimal due to factors such as device position, change in physiological state, etc.

Figure 7:
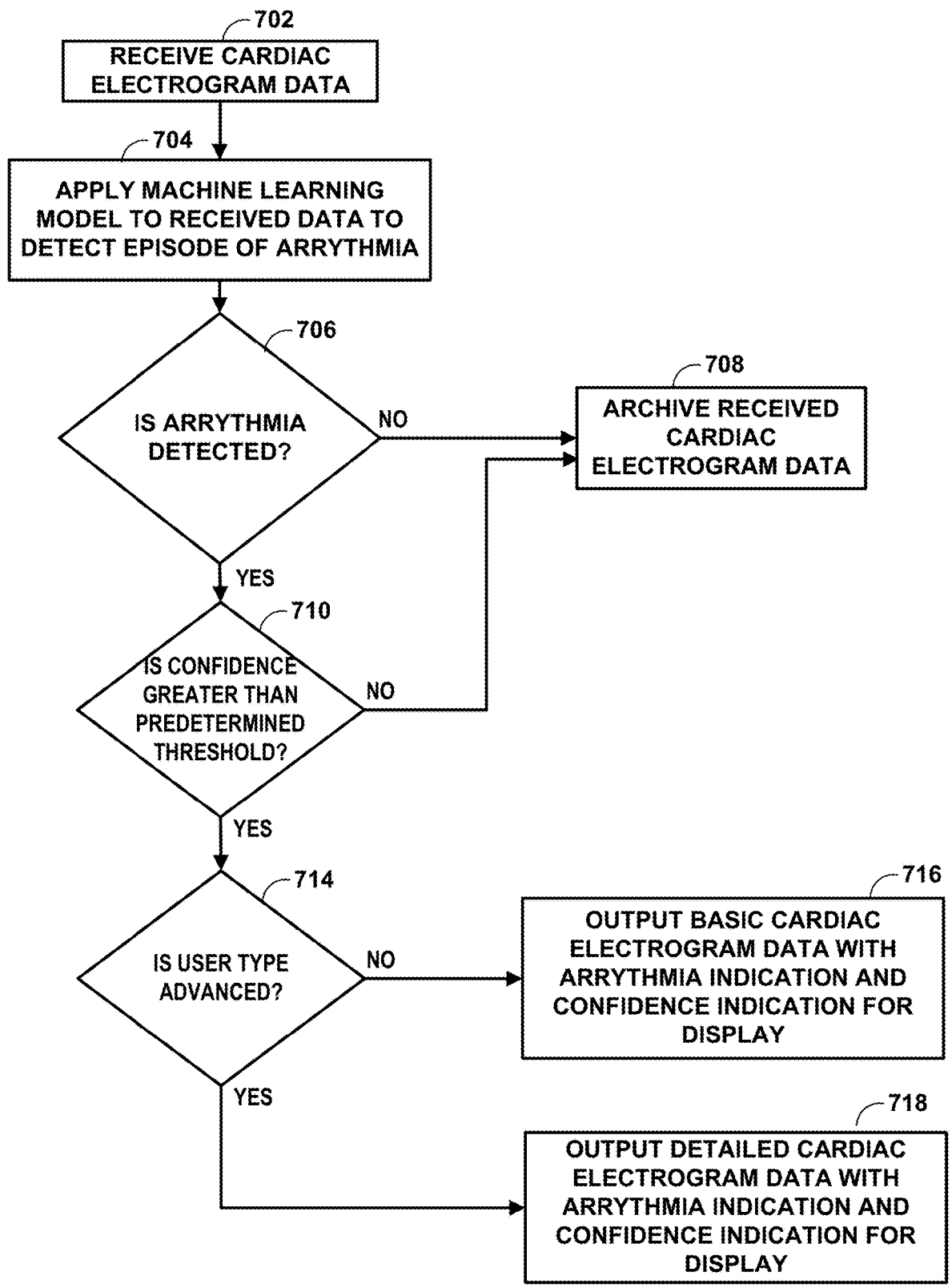
FIG. 7 is a flowchart illustrating an example operation in accordance with the techniques of the disclosure.

FIG. 7 is a flowchart illustrating an example operation in accordance with the techniques of the disclosure. For convenience, FIG. 7 is described with respect to FIG. 1. In some examples, the operation of FIG. 7 is an operation for explaining and visualizing an output of machine learning system 150 that detects an episode of cardiac arrhythmia in patient 4.

Computing system 24 receives the cardiac electrogram data from external device 12 (702). Machine learning system 150 of computing system 24 applies a machine learning model to the received cardiac electrogram data to detect an episode of arrhythmia in patient 4 (704). Computing system 24 determines whether an episode of arrhythmia is detected (706), and a level of confidence in the detection (710). The operation of steps 702, 704, 706, 708, and 710 may occur in a substantially similar fashion as steps 502, 504, 506, 508, and 510 of FIG. 5, respectively.

Furthermore, computing system 24 determines whether a user type is advanced (714).

In this example, computing system 24 may customize the visualization of the cardiac electrogram data based on the ability of the user. For example, computing system 24 may present more- or less-detailed ECG waveform, metadata, and resulting analysis provided by the AI as needed for a variety of users of different abilities.

For example, in response to determining that the user type is not advanced (e.g., a basic user type) (e.g., "NO" block of 714), computing system 24 outputs basic cardiac electrogram data, a first indication that the episode of arrhythmia has occurred in patient 4, and a second indication of the level of certainty in the determination that the episode of arrhythmia has occurred in patient 4 (716). For example, for non-experts such as implanting cardiologists, neurologists, HF physicians, device nurses, patients/caregivers, computing system 24 may present for display an overall performance of machine learning system 150 in terms of a "true and false" positive detection of an episode of arrhythmia. In some examples, computing system 24 may further present, for display, an ECG segment depicting the detected episode of arrhythmia overlaid with a representative episode of arrhythmia of the same classification (e.g., an ECG segment of patient 4 presenting AF overlaid with a representative example waveform of AF). In some examples, computing system 24 may further present, for display, an ECG segment depicting the detected episode of arrhythmia overlaid with a baseline or non-AF episode. In some examples, computing device 24 presents, to a basic user, an ECG waveform of the patient, a first representation of a first ECG waveform presenting an episode of arrhythmia, and a second representation of a second ECG waveform presenting normal cardiac behavior.

As another example, in response to determining that the user type is advanced (e.g., "YES" block of 714), computing system 24 outputs advanced cardiac electrogram data, the first indication that the episode of arrhythmia has occurred in patient 4, and the second indication of the level of certainty in the determination that the episode of arrhythmia has occurred in patient 4 (718). For example, for an electrophysiologist or subject matter expert, computing system 24 may display, e.g. for an episode of AF, a start and stop time of each episode of arrhythmia presented along with a mean RR during each AF segment contrasted against a mean RR baseline, an RR variation during each AF segment contrasted against an RR variation baseline, P-wave evidence during the AF segment contrasted with a P-wave baseline, and morphology variation. Computing system 24 may present additional types of information not expressly described herein to improve a confidence of the expert in machine learning system 150 and to assist the expert in interpreting an episode of cardiac arrhythmia. In some examples, computing device 24 presents, to an advanced user, one or more of an ECG waveform of patient 4, a start time of the episode of arrhythmia, a stop time of the episode of arrhythmia, a mean R-R interval of patient 4 during the episode of arrhythmia, an R-R variation of patient 4 during the episode of arrhythmia, a baseline R-R interval of patient 4, a P-wave of patient 4 during the episode of arrhythmia, a baseline P-wave of patient 4, or a morphology variation of patient 4.

Accordingly, the operation of FIG. 7 further allows for a different data presentation based upon the skill, ability, or experience of the user accessing the data. The operation of FIG. 7 may be used, e.g., in situations where a patient is prescribed a cardiac monitor by a physician stakeholder that is less familiar with interpretation of cardiac waveforms (e.g., a clinician who is not a cardiologist or subject matter expert), but whom still wants to see a basic presentation of the characteristics of the cardiac electrogram data and/or the classification by machine learning system 150. By using the techniques of the disclosure, a medical device system such as medical device system 2 may provide an end-user with an appropriate amount of data. Thus, medical device system 2 may enable a clinician to make an appropriate diagnosis or referral, or to confirm the presence or absence of an expected cardiac rhythm (or arrhythmia). Furthermore, medical device system 2 may avoid burdening a clinician with data irrelevant to their required level of understanding.

Figure 8:
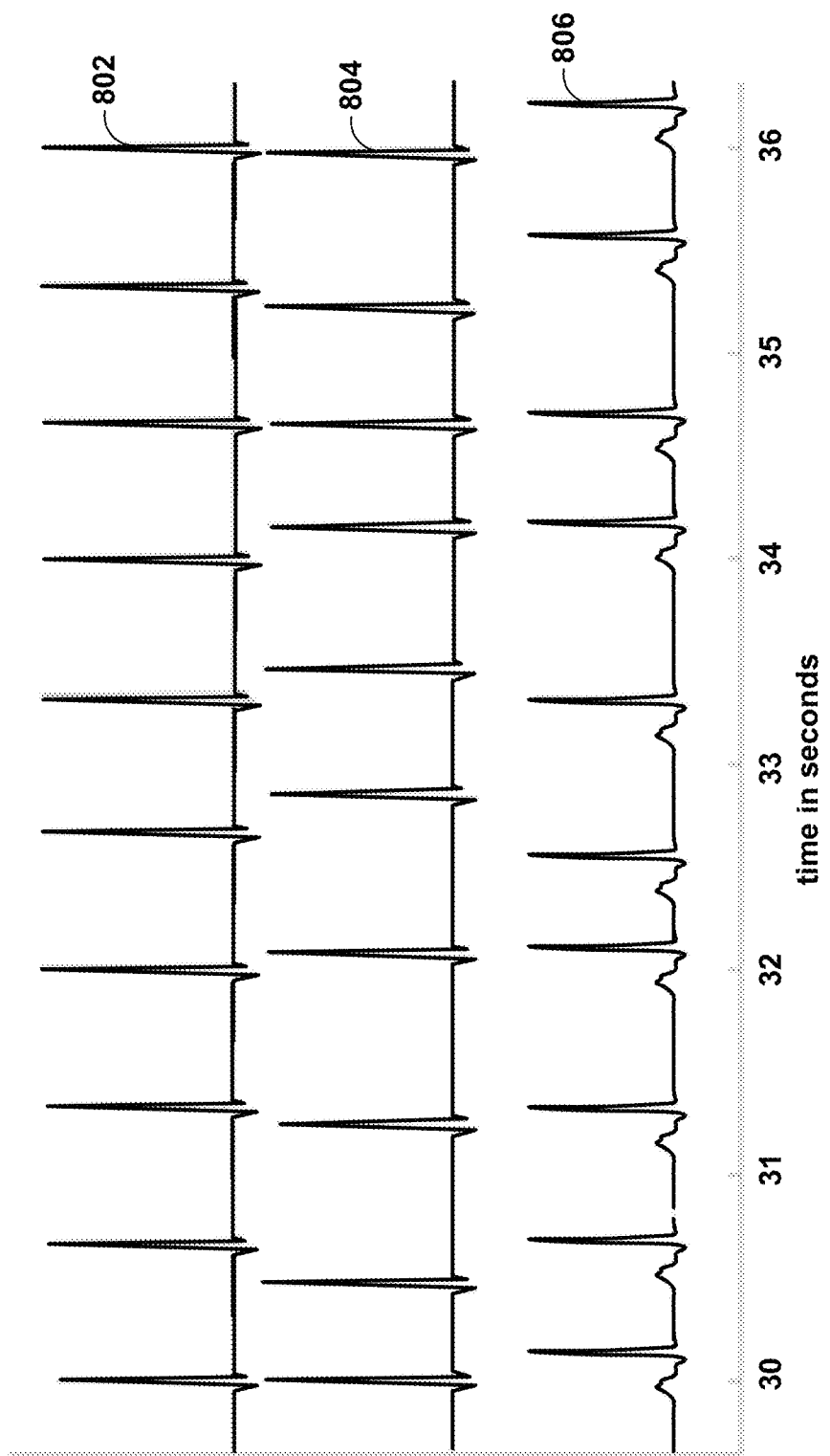
FIG. 8 is a graph illustrating example simulated cardiac electrogram data that may be used to explain a machine learning system in accordance with the techniques of the disclosure.

FIG. 8 is a graph illustrating example simulated cardiac electrogram data that may be used to explain machine learning system 150 in accordance with the techniques of the disclosure. For convenience, FIG. 8 is described with respect to medical system 24 of FIG. 1.

Unlike feature-engineered algorithms, it may not be clear exactly how machine learning system 150 operates to detect arrhythmia from cardiac electrogram data of a patient. As described herein, computing system 24 may use simulated cardiac electrogram data, such as waveforms 802, 804, and 806, to probe different aspects of the arrhythmia characterization performed by machine learning system 150. For example, computing system 24 may feed simulated cardiac electrogram data across a plurality of different characteristics to machine learning system 150 and map the output of machine learning system 150 (as described in more detail below with respect to FIGS. 9A-9C) to understand how the machine learning model weighs the different characteristics as more or less important with respect to detecting arrhythmia of a particular type. For example, computing system 24 may use simulated cardiac electrogram data that has differing values for RR variability (RRV), RR rate, or p-waves to examine how machine learning system 150 characterizes AF. As described herein, "RRV" refers to a variation in the interval between successive "R" points corresponding to peak of a QRS complex of an ECG wave. By using the simulated cardiac electrogram data and the determination by the machine learning system 150 of a likelihood of arrhythmia for different portions of the simulated cardiac electrogram data, computing system 24 may explain the operation of machine learning system 150. While examples specific to Normal Sinus Rhythm (NSR), Bradyarrhythmia, and AF are described herein, the techniques of the disclosure may be used for other types of arrhythmia as well.

In one example, computing system 24 receives a dataset of waveforms with the following characteristics:
- Mean heart rate (HR) ranging from 40 beats per minute (BPM) to 120 BPM;
- RRV for the waveform ranging from 0.01 seconds to 0.5 seconds; and
- QRS complex with p-waves and without p-waves.

In other words, computing system 24 "explains" the analysis of machine learning system 150 based on characteristics of the simulated cardiac electrogram data such as these, which may be more understandable by experts in the field and have "real-world" significance.

In some examples, computing system 24 may use simulated data for at least a portion of the mean heart rate data, the RRV data, or the QRS complex where such data is unavailable. For example, patient 4 may not exhibit an entire range of parameters required to explain the model (e.g, such as BPM less than 50). The use of such simulated data may allow computing system 24 to explain the analysis of machine learning system 150 without requiring edge-case data from patient 4 that is difficult or infeasible to obtain. In some examples, computing system 24 may use real data for patient 4 where such data is available.

The example of FIG. 8 depicts 3 example waveforms 802, 804, and 806. Waveform 802 is a waveform with a mean heartrate of 90 BPM and an RR variability of 0.01 seconds. Waveform 804 is a waveform with a mean heartrate of 90 BPM and an RR variability of 0.01 seconds. Waveform 806 is a waveform with a mean heartrate of 90 BPM, an RR variability 0.5 seconds and p-waves. In some examples, at least a portion of one or more of waveforms 802, 804, and 806 may be obtained from simulated data.

Machine learning system 150 processes each of waveforms 802, 804, and 806 and outputs a likelihood that an arrhythmia occurrence in the [0,1] range was extracted. A likelihood close to 0 indicates that an episode of arrhythmia in the waveform is unlikely, and a likelihood close to 1 that an episode of arrhythmia in the waveform is very likely. Computing system 24 may use such information to explain, e.g., at what heartrates machine learning system 150 detects an episode of arrhythmia of a particular type (e.g., AF), at what RRV machine learning system 150 detects an episode of arrhythmia of a particular type (e.g., AF), or at what p-wave levels machine learning system 150 detects an episode of arrhythmia of a particular type (e.g., AF).

Figure 9A:
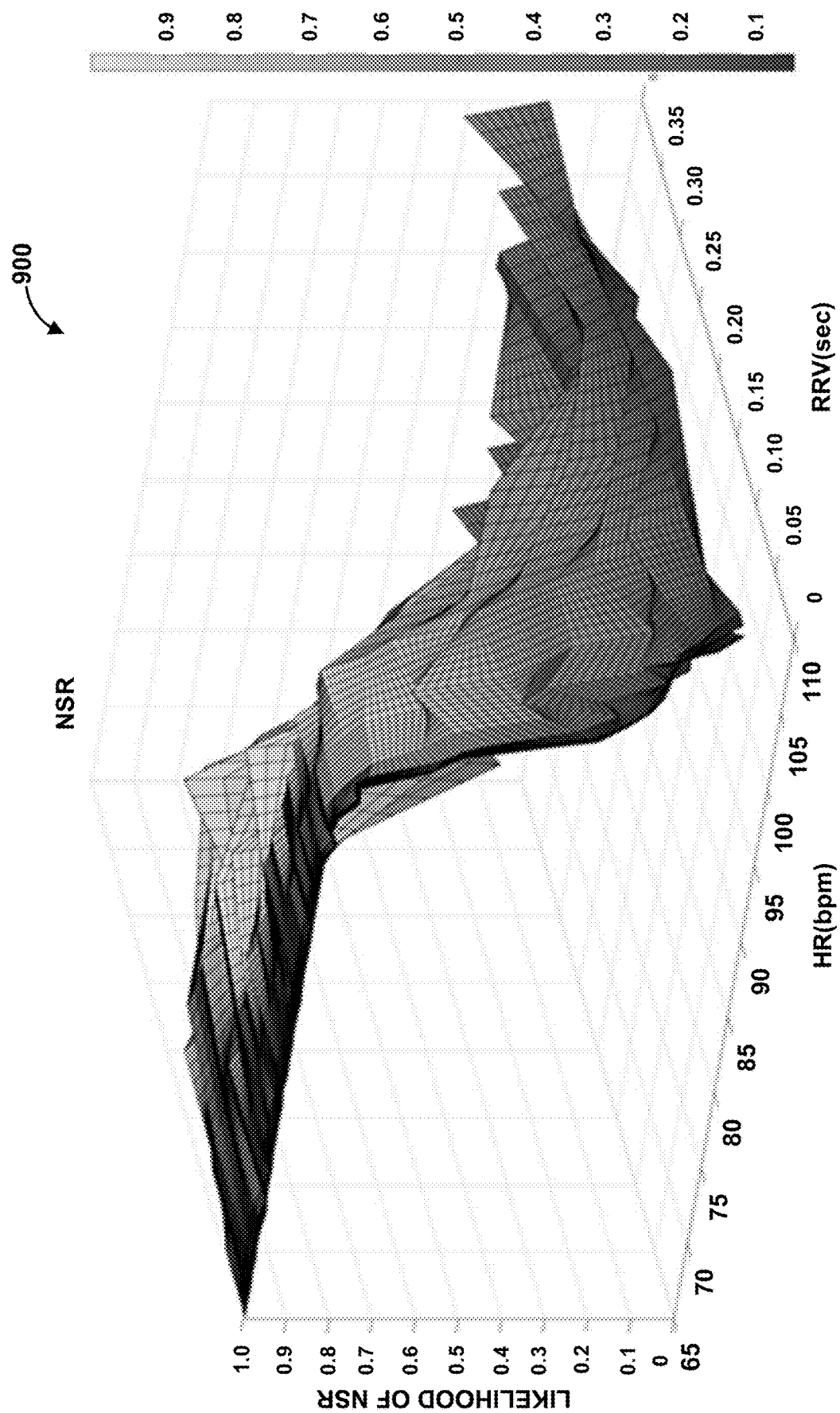
FIGS. 9A-9C are graphs illustrating techniques for visualizing the operation of machine learning model 150 of FIG. in detecting an episode of arrhythmia in accordance with the techniques of the disclosure.
Figure 9B:
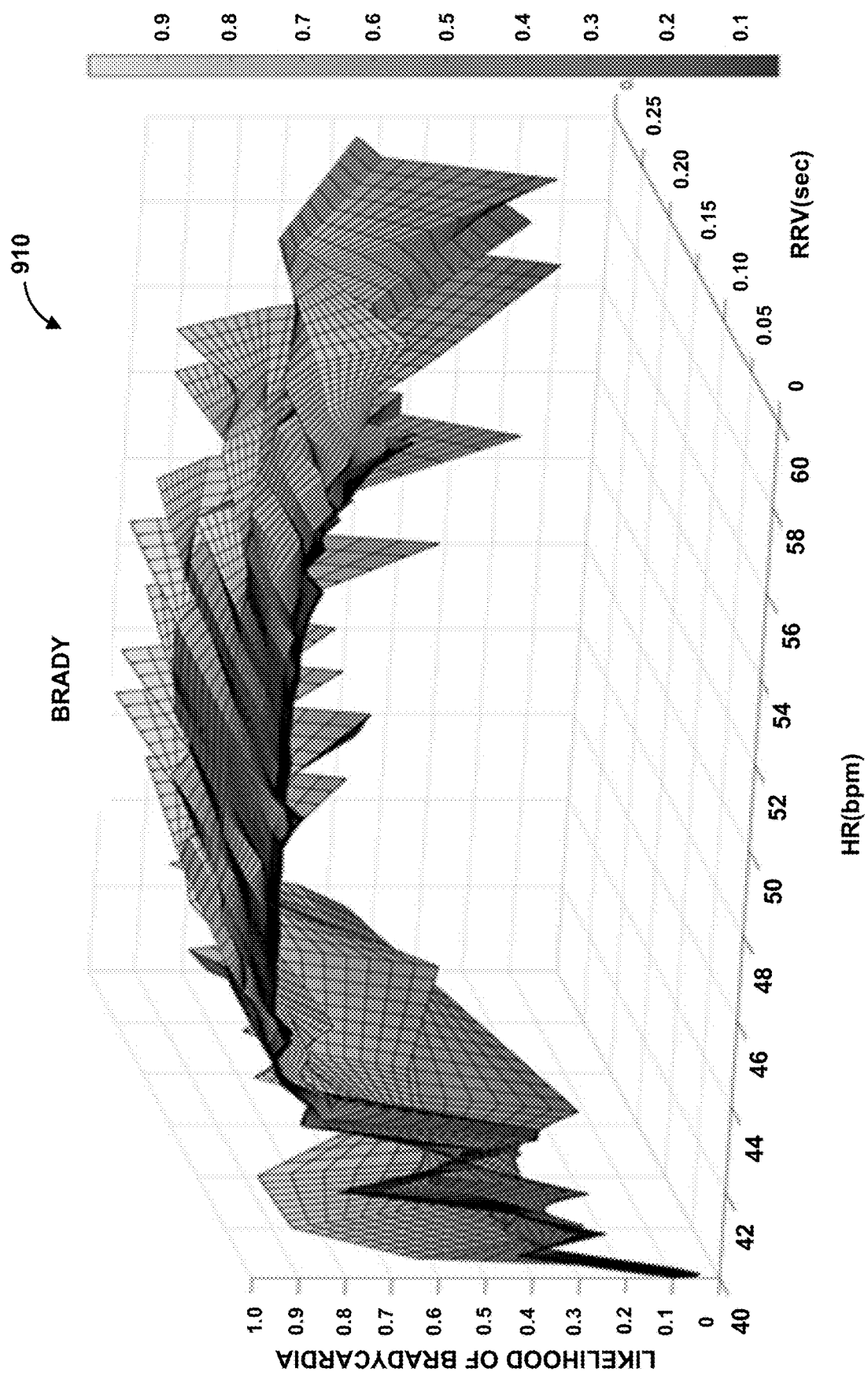
Figure 9C:
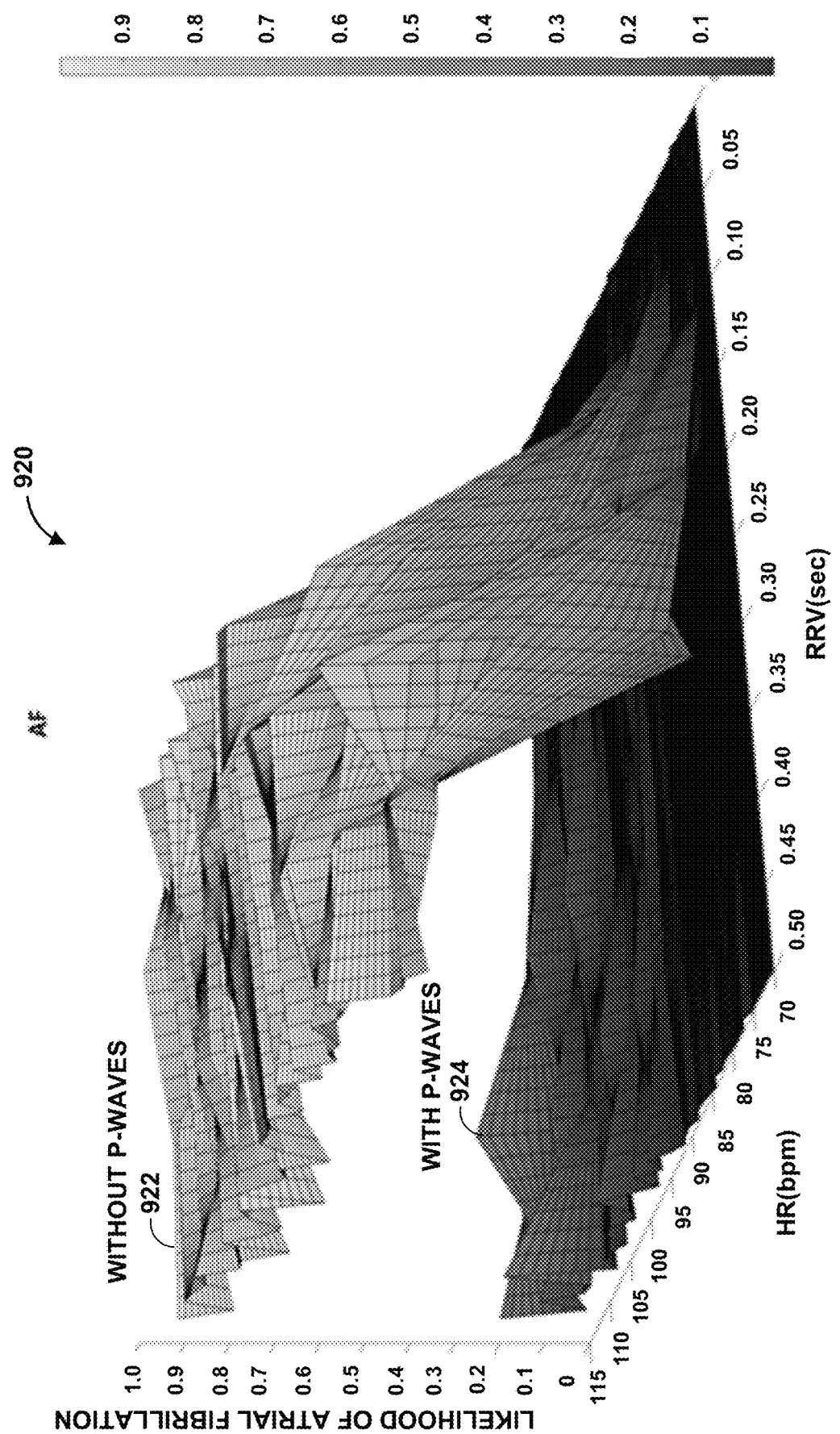

FIGS. 9A-9C are graphs illustrating techniques for visualizing the operation of machine learning model 150 of FIG. in detecting an episode of arrhythmia in accordance with the techniques of the disclosure. In some examples, FIGS. 9A-9C illustrate an explanation by computing system 24 of an analysis by machine learning system 150 of the example waveforms 802, 804, and 806 of FIG. 8. By presenting the output of machine learning system 150 with respect to the simulated cardiac electrogram data of FIG. 8, computing system 24 may explain the operation of machine learning system 150 with respect to different characteristics of the simulated cardiac electrogram data.

FIG. 9A depicts an example graphical illustration 900 of a likelihood that machine learning system 150 predicts a normal sinus rhythm (NSR) in patient 4. For example, FIG. 9B depicts a likelihood that machine learning system 150 detects NSR as a function of mean heartrate. The y-axis of FIG. 9A depicts a likelihood determined by machine learning system 150 that NSR is present, on a scale of 0% to 100%. A color of FIG. 9A may correspond to the value of the y-axis (e.g., with yellow corresponding to high likelihood that NSR is present and blue corresponding to low likelihood that NSR is present). The x-axis of FIG. 9A depicts a heart rate in beats per minute (BPM), and the z-axis of FIG. 9A depicts an RRV in seconds. As illustrated in FIG. 9A, machine learning system 150 detects NSR where the cardiac electrogram has an RRV less than 0.1 and a heartrate between 65 and 85 BPM. A clinician may use such information to characterize how normal sinus rhythms in patient 4 are annotated. For example, the machine learning model described in FIG. 9A was developed with data from a specific clinic that considers heartrates between 65 and 85 BPM to be NSR.

FIG. 9B depicts an example graphical illustration 910 of a likelihood that machine learning system 150 detects bradycardia. For example, FIG. 9B depicts a likelihood that machine learning system 150 detects bradycardia as a function of mean heartrate. The y-axis of FIG. 9B depicts a likelihood determined by machine learning system 150 that bradycardia is present, on a scale of 0% to 100%. A color of FIG. 9B may correspond to the value of the y-axis (e.g., with yellow corresponding to high likelihood that bradycardia is present and blue corresponding to low likelihood that bradycardia is present). The x-axis of FIG. 9B depicts a heart rate in BPM, and the z-axis of FIG. 9B depicts an RRV in seconds. As illustrated in FIG. 9B, machine learning system 150 detects sinus bradycardia where the cardiac electrogram has an RRV less than 0.1 and a heartrate between 45 and 55 BPM. A clinician may use such information to characterize how episodes of bradycardia in patient 4 are annotated. For example, the machine learning model described in FIG. 9B was developed with data from a specific clinic that considers heartrates between 45 and 55 BPM to be sinus bradycardia.

FIG. 9C depicts an example graphical illustration 920 of a likelihood that machine learning system 150 detects atrial fibrillation (AF). The example of FIG. 9C depicts a likelihood that machine learning system 150 detects AF a function of mean heartrate, RR variability and P-waves. The y-axis of FIG. 9C depicts a likelihood determined by machine learning system 150 that AF is present on a scale of 0% to 100%. A color of FIG. 9C may correspond to the value of the y-axis (e.g., with yellow corresponding to high likelihood that AF is present and blue corresponding to low likelihood that AF is present). The x-axis of FIG. 9C depicts a heart rate in BPM, and the z-axis of FIG. 9C depicts RRV in seconds. Further, FIG. 9C depicts two scenarios: where p-waves are present (924) and where p-waves are absent (922). As illustrated in FIG. 9C, machine learning system 150 detects AF where the cardiac electrogram has an RRV greater than 0.2, a heartrate greater than 75 BPM, and p-waves are absent. In the presence of p-waves, machine learning system 150 does not detect AF. While not depicted in FIG. 9C, machine learning system 150 may detect episodes of PAC more often in the presence of p-waves. A clinician may use such information to characterize how episodes of AF in patient 4 are annotated. For example, the machine learning model described in FIG. 9C was developed with data from a specific clinic that considers heartrates greater than 75 BPM and RRV greater than 0.2 to be AF.

The example visualization techniques depicted by FIGS. 9A-9C may be extended by including other deep-learning visualization techniques. For example, the techniques of the disclosure may readily be adapted to deep-learning techniques for visualizing deep network features or for visualizing neural style transfer. Furthermore, the techniques of the disclosure may be adapted to visualize other types of cardiac arrhythmia not expressly depicted in FIGS. 9A-9C, such as ventricle fibrillation or AV Block.

Figure 10A:
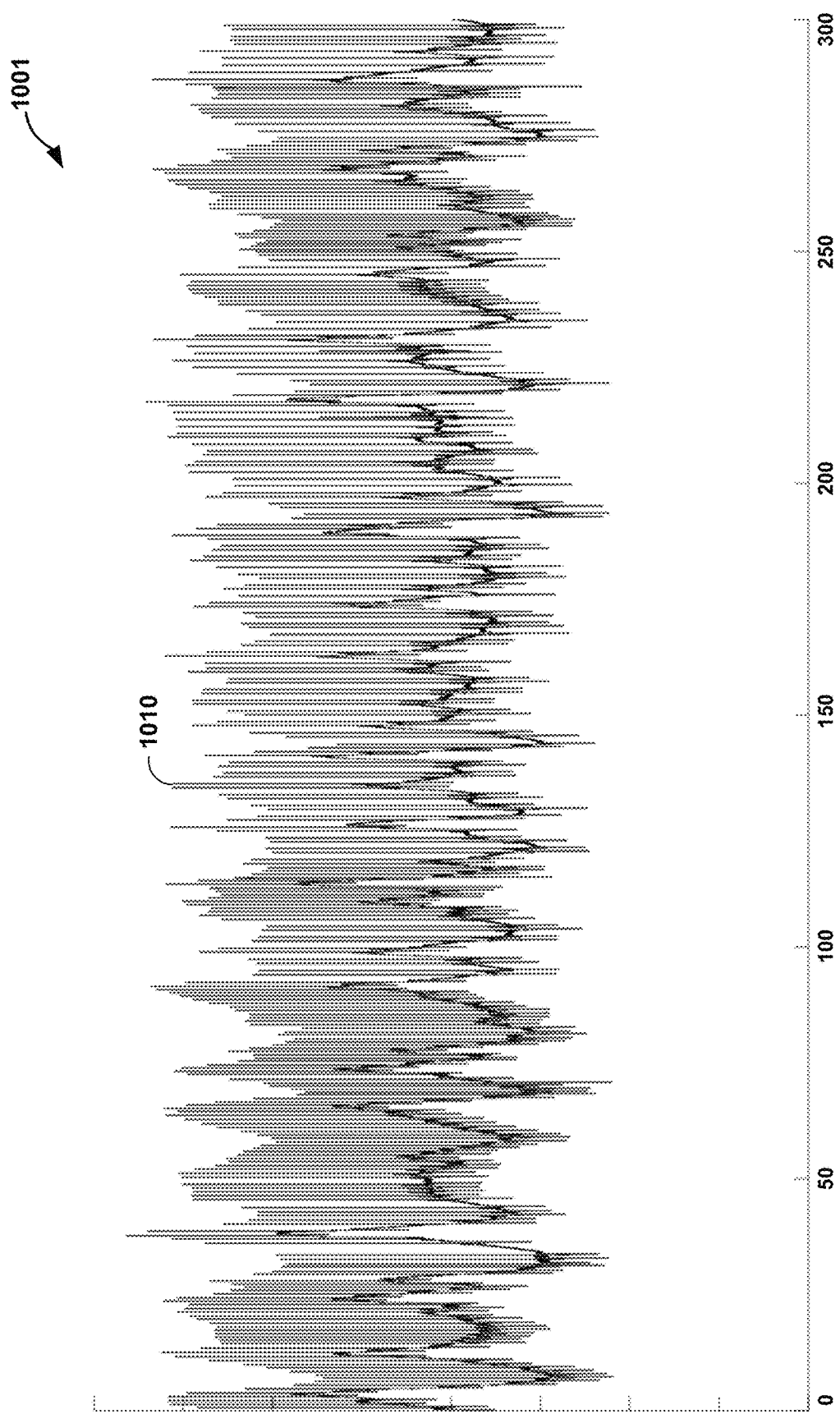
FIGS. 10A-10D are illustrations depicting an example display for visualizing cardiac electrogram data of a patient by a medical device in accordance with the techniques of the disclosure.

FIGS. 10A-10D are illustrations depicting example displays 1001-1004 for visualizing cardiac electrogram data 1010 of patient 4 by a computing device in accordance with the techniques of the disclosure. Cardiac electrogram data 1010 may be sensed by, e.g., IMD 10 as described above. Display 1000 may be presented, e.g., by computing system 24 or by external device 12. FIG. 10A depicts display 1001 presenting cardiac electrogram data 1010 of patient 4 sensed by IMD 10.

Figure 10B:
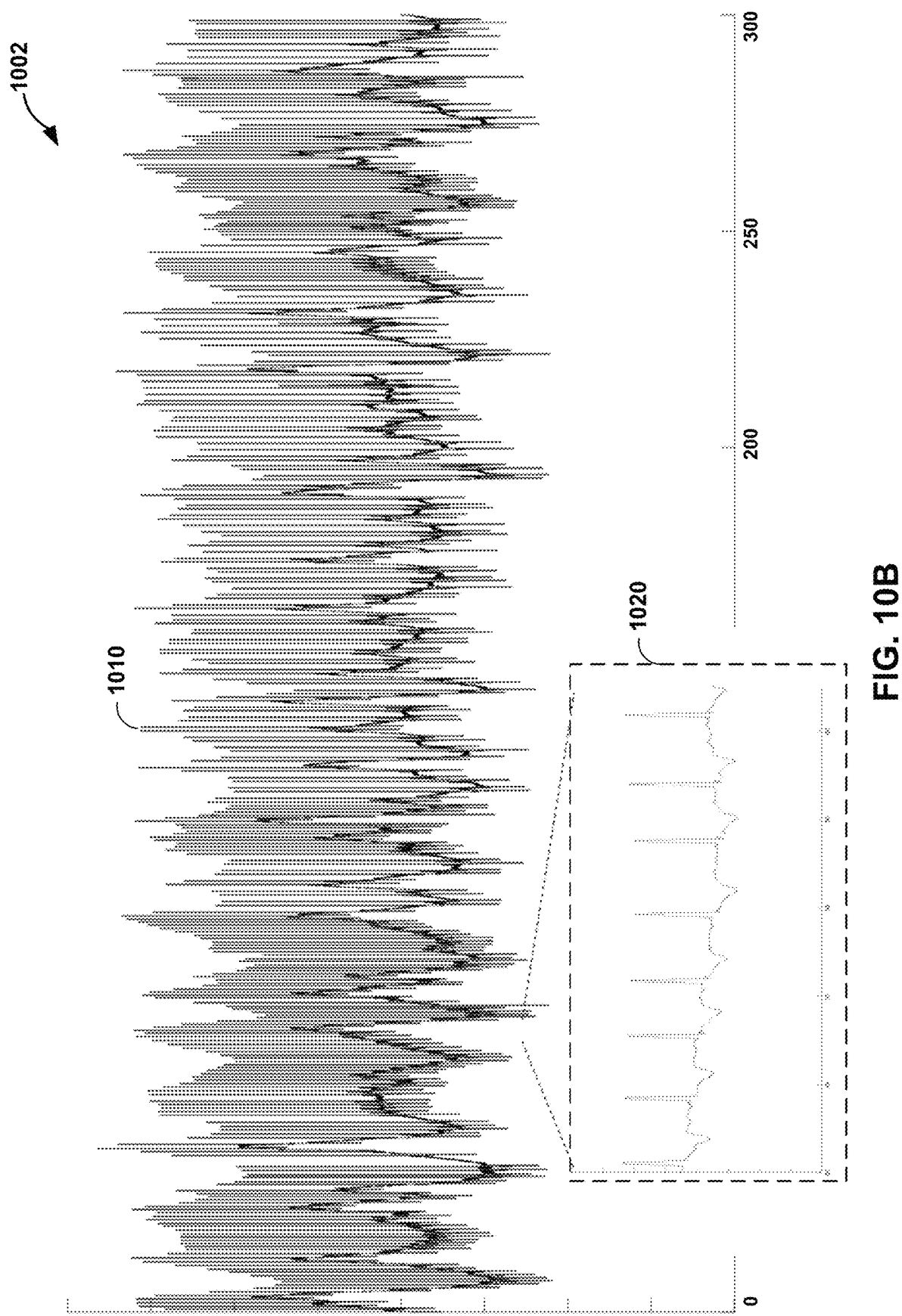

FIG. 10B depicts display 1002 presenting basic cardiac information, e.g., ECG segment 1020 of cardiac electrogram data 1010 during which computing system 24 has determined that an episode of arrhythmia in patient 4 has occurred. In some examples, ECG segment 1020 is a segment of cardiac electrogram data 1010 in which computing system 24 has determined is the highest likelihood as presenting an episode of atrial fibrillation in patient 4. The example presentation of FIG. 10B may be used, e.g., when a user is a basic user that does not need comprehensive information regarding the determination of the episode of arrhythmia by computing system 24.

Figure 10C:
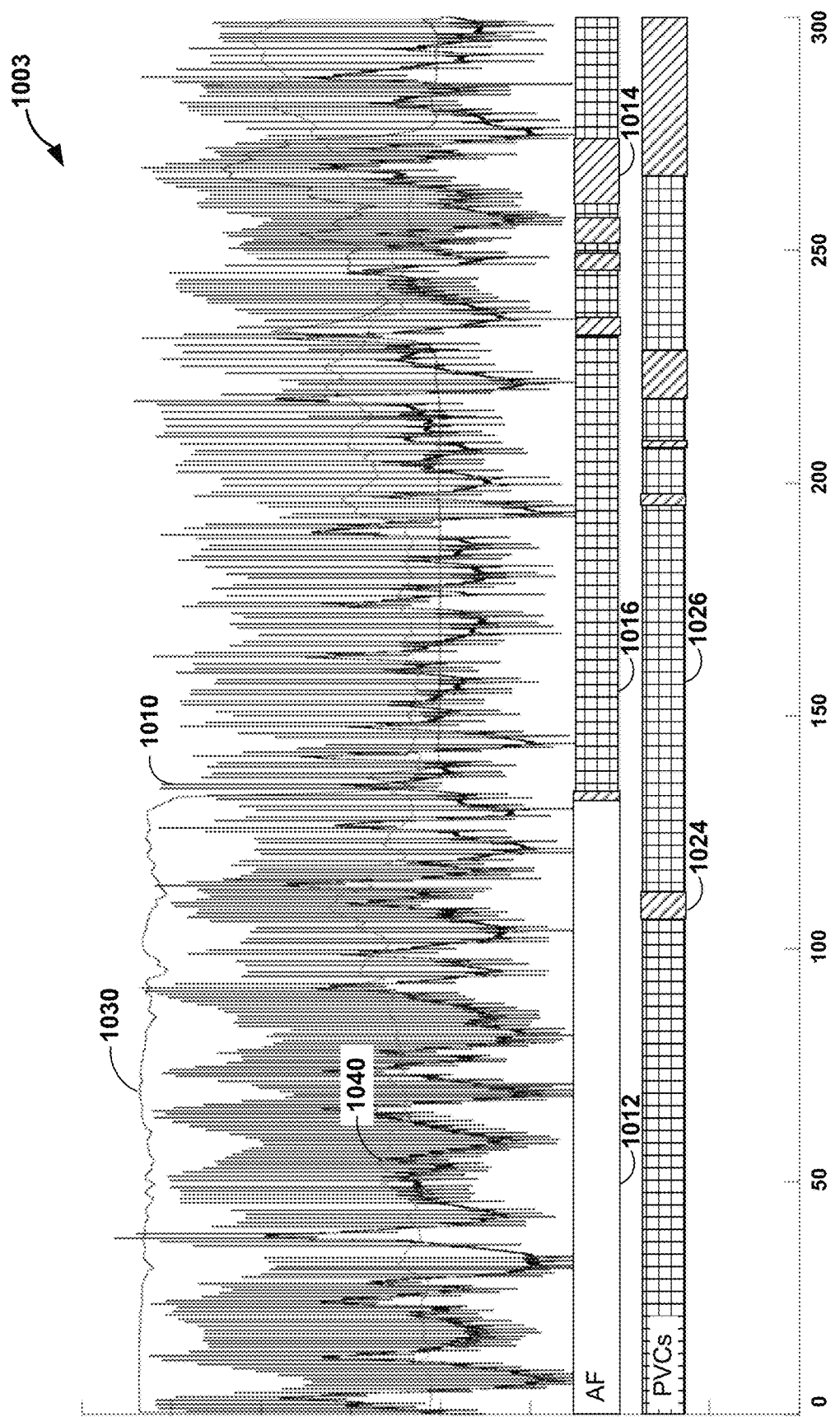

FIG. 10C depicts display 1003 presenting advanced cardiac information. For example, display 1003 includes cardiac electrogram data 1010 and further depicts, for a plurality of segments of cardiac electrogram data 1010, a likelihood that an episode of cardiac arrhythmia of one or more types has occurred. For example, display 1003 colors segments for which computing system 24 has determined a high likelihood that atrial fibrillation has occurred in patient 4 in green (1012), segments for which computing system 24 has made an uncertain determination of whether atrial fibrillation has occurred in patient 4 in yellow (1014), and segments for which computing system 24 has determined a low likelihood that atrial fibrillation has occurred in patient 4 in red (1016). Furthermore, display 1003 depicts an overall likelihood 1030 that atrial fibrillation has occurred in patient 4 over time in blue.

As another example, display 1003 colors segments for which computing system 24 has determined a high likelihood that PVC has occurred in patient 4 in green (no episodes in FIG. 10C), segments for which computing system 24 has made an uncertain determination of whether PVC has occurred in patient 4 in yellow (1024), and segments for which computing system 24 has determined a low likelihood that PVC has occurred in patient 4 in red (1026). Furthermore, display 1003 depicts an overall likelihood 1040 that PVC has occurred in patient 4 over time in magenta.

Figure 10D:
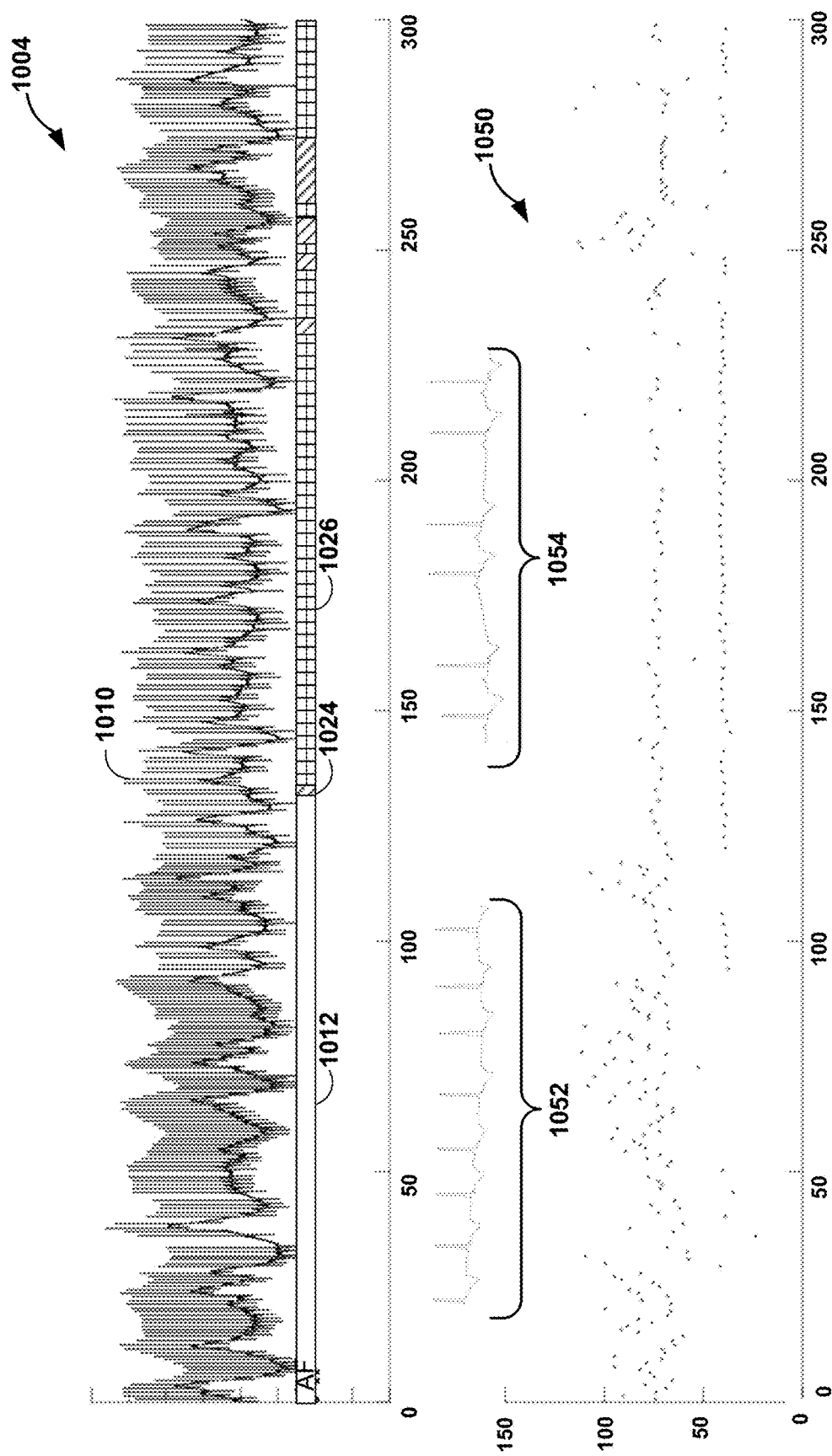

FIG. 10D depicts display 1004 presenting advanced cardiac information. For example, display 1004 depicts information substantially similar to display 1003 of FIG. 10C. Further, display 1004 further depicts reference cardiac electrogram data 1054 that depicts a baseline ECG signal (e.g., where no AF is present) and reference cardiac electrogram data 1052 that depicts an ECG signal during an episode of AF. Furthermore, display 1004 includes RR interval diagram 1050, which displays RR intervals of patient 4 over the duration of cardiac electrogram data 1010. RR interval diagram 1050 demonstrates high, un-patterned RR variability during the presence of AF (e.g., from time t0 to about time t100) and patterned beats during a lack of AF (e.g., from time t150 to time t250). The example presentations of FIG. 10C or 10D may be used, e.g., when a user is an advanced basic user that desires comprehensive information regarding the determination of the episode of arrhythmia by computing system 24.

Figure 11A:
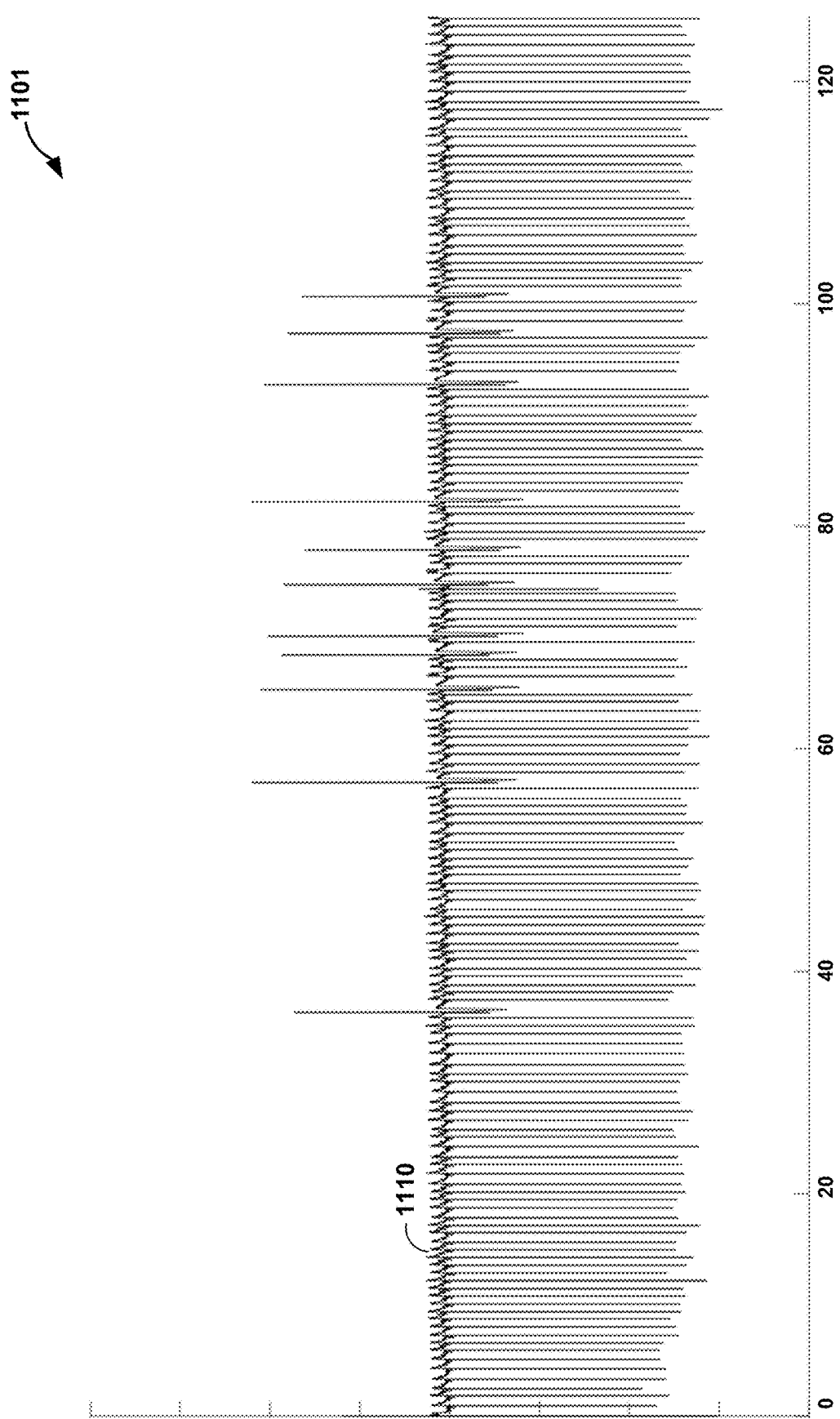
Figure 11C:
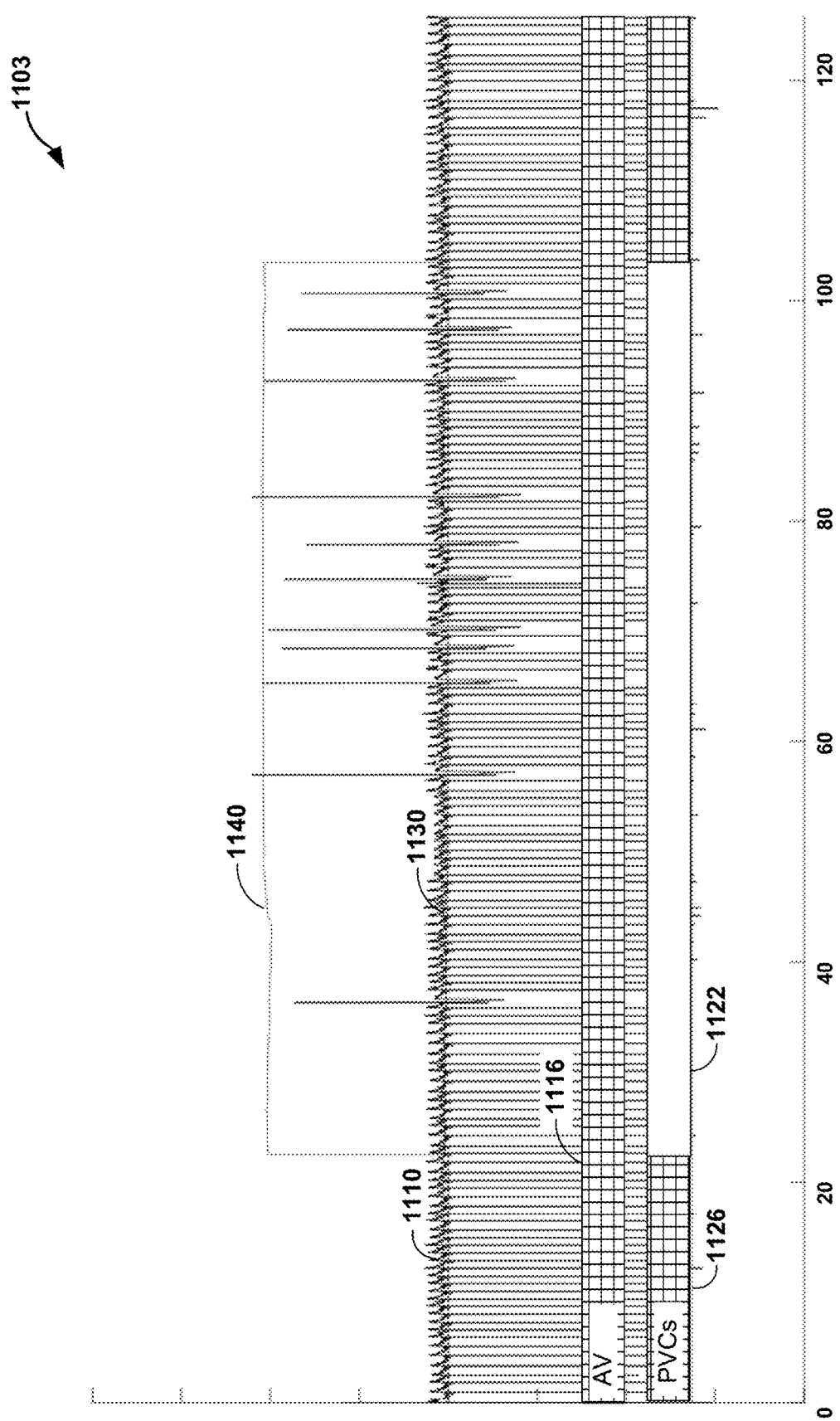

FIGS. 11A-11C are illustrations depicting an example displays 1101-1103 for visualizing cardiac electrogram data 1110 of patient 4 by a computing device in accordance with the techniques of the disclosure. Cardiac electrogram data 1110 may be sensed by, e.g., IMD 10 as described above. Display 1100 may be presented, e.g., by computing system 24 or by external device 12. FIG. 11A depicts display 1101 presenting cardiac electrogram data 1110 of patient 4 sensed by IMD 10.

FIG. 11B depicts display 1102 presenting basic cardiac information, e.g., ECG segment 1120 of cardiac electrogram data 1110 during which computing system 24 has determined that an episode of arrhythmia in patient 4 has occurred. In some examples, ECG segment 1120 is a segment of cardiac electrogram data 1110 in which computing system 24 has determined is the highest likelihood as presenting an episode of PVC in patient 4. The example presentation of FIG. 11B may be used, e.g., when a user is a basic user that does not need comprehensive information regarding the determination of the episode of arrhythmia by computing system 24.

FIG. 11C depicts display 1103 presenting advanced cardiac information. For example, display 1103 includes cardiac electrogram data 1110 and further depicts, for a plurality of segments of cardiac electrogram data 1110, a likelihood that an episode of cardiac arrhythmia of one or more types has occurred. For example, display 1103 colors segments for which computing system 24 has determined a high likelihood that atrial fibrillation has occurred in patient 4 in green (not present in FIG. 11C), segments for which computing system 24 has made an uncertain determination of whether atrial fibrillation has occurred in patient 4 in yellow (not present in FIG. 11C), and segments for which computing system 24 has determined a low likelihood that atrial fibrillation has occurred in patient 4 in red (1116). Furthermore, display 1103 depicts an overall likelihood 1130 that atrial fibrillation has occurred in patient 4 over time in blue.

As another example, display 1103 colors segments for which computing system 24 has determined a high likelihood that PVC has occurred in patient 4 in green (1122), segments for which computing system 24 has made an uncertain determination of whether PVC has occurred in patient 4 in yellow (not present in FIG. 11C), and segments for which computing system 24 has determined a low likelihood that PVC has occurred in patient 4 in red (1126). Furthermore, display 1103 depicts an overall likelihood 1140 that PVC has occurred in patient 4 over time in magenta.

The following examples may illustrate one or more aspects of the disclosure.

Example 1

A method comprising: receiving, by a computing device comprising processing circuitry and a storage medium, cardiac electrogram data sensed by a medical device; applying, by the computing device, a machine learning model, trained using cardiac electrogram data for a plurality of patients, to the received cardiac electrogram data to: determine, based on the machine learning model, that an episode of arrhythmia has occurred in the patient; and determine a level of confidence in the determination that the episode of arrhythmia has occurred in the patient; determining that the level of confidence in the determination that the episode of arrhythmia has occurred in the patient is greater than a predetermined threshold; and in response to determining that the level of confidence is greater than the predetermined threshold, outputting, by the computing device and for display to a user, at least a portion of the cardiac electrogram data, a first indication that the episode of arrhythmia has occurred in the patient, and a second indication of the level of confidence that the episode of arrhythmia has occurred in the patient.

Example 2

The method of example 1, wherein the at least a portion of the cardiac electrogram data comprises an electrocardiogram (ECG) waveform.

Example 3

The method of example 2, wherein the first indication that the episode of arrhythmia has occurred in the patient comprises an annotation to the ECG waveform.

Example 4

The method of any of examples 1 through 3, wherein the second indication comprises one or more of a color, an image, a light, a sound, or a textual notification.

Example 5

The method of any of examples 1 through 4, wherein the method further comprises receiving, from the user, a selection of an arrhythmia type, wherein applying the machine learning model to the received cardiac electrogram data to determine that an episode of arrhythmia has occurred in the patient comprises applying the machine learning model to the received cardiac electrogram data to determine that an episode of arrhythmia of the selected arrhythmia type has occurred in the patient, and wherein outputting the at least a portion of the cardiac electrogram data, the first indicator that the episode of arrhythmia has occurred in the patient, and the second indicator of the level of confidence that the episode of arrhythmia has occurred in the patient comprises outputting the at least a portion of the cardiac electrogram data, a first indicator that the episode of arrhythmia of the selected arrhythmia type has occurred in the patient, and the second indicator of the level of confidence that the episode of arrhythmia of the selected arrhythmia type has occurred in the patient.

Example 6

The method of any of examples 1 through 5, wherein the method further comprises determining, by the computing device, that the user is a basic user, wherein, outputting the at least a portion of the cardiac electrogram data, the first indicator that the episode of arrhythmia has occurred in the patient, and the second indicator of the level of confidence that the episode of arrhythmia has occurred in the patient comprises outputting, in response to determining that the user is a basic user, the first indicator that the episode of arrhythmia has occurred in the patient, the second indicator of the level of confidence that the episode of arrhythmia has occurred in the patient, and one or more of: an electrocardiogram (ECG) waveform of the patient; a first representation of a first ECG waveform presenting an episode of arrhythmia; and a second representation of a second ECG waveform presenting normal cardiac behavior.

Example 7

The method any of examples 1 through 5: wherein the method further comprises determining, by the computing device, that the user is an advanced user, wherein, outputting the at least a portion of the cardiac electrogram data, the first indicator that the episode of arrhythmia has occurred in the patient, and the second indicator of the level of confidence that the episode of arrhythmia has occurred in the patient comprises outputting, in response to determining that the user is an advanced user, the first indicator that the episode of arrhythmia has occurred in the patient, the second indicator of the level of confidence that the episode of arrhythmia has occurred in the patient, and one or more of: an electrocardiogram (ECG) waveform of the patient; a start time of the episode of arrhythmia; a stop time of the episode of arrhythmia; a mean R-R interval of the patient during the episode of arrhythmia; an R-R variation of the patient during the episode of arrhythmia; a baseline R-R interval of the patient; a P-wave of the patient during the episode of arrhythmia; a baseline P-wave of the patient; and a morphology variation of the patient.

Example 8

The method of any of examples 1 through 7, wherein the episode of arrhythmia in the patient is at least one of an episode of bradycardia, tachycardia, atrial fibrillation, ventricular fibrillation, or AV Block.

Example 9

The method of any of examples 1 through 8, wherein the machine learning model trained using cardiac electrogram data for the plurality of patients comprises a machine learning model trained using a plurality of electrocardiogram (ECG) waveforms, each ECG waveform labeled with one or more episodes of arrhythmia in a patent of the plurality of patients.

Example 10

The method of any of examples 1 through 9, wherein applying the machine learning model to the received cardiac electrogram data comprises applying the machine learning model to at least one of: electrocardiogram (ECG) data of the patient; the characteristics correlated to arrhythmia in the patient; a type of the arrhythmia in the patient; an activity level of the implantable medical device; an input impedance of the implantable medical device; or a battery level of the implantable medical device.

Example 11

The method of any of examples 1 through 10, wherein outputting the at least a portion of the cardiac electrogram data comprises: identifying a subsection of an electrocardiogram (ECG) of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods; and outputting the subsection of the ECG.

Example 12

The method of any of examples 1 through 11, wherein the predetermined threshold is a first predetermined threshold, and wherein the method further comprises determining whether the level of confidence in the determination that the episode of arrhythmia has occurred in the patient is greater than a second predetermined threshold, the second predetermined threshold greater than the first predetermined threshold, wherein in response to determining that the level of confidence is greater than the predetermined threshold, outputting, the at least a portion of the cardiac electrogram data, the first indication, and the second indication comprises: in response to determining that the level of confidence is greater than the first predetermined threshold but not greater than the second predetermined threshold, outputting, the at least a portion of the cardiac electrogram data, the first indication, and an indication of a medium level of confidence that the episode of arrhythmia has occurred in the patient; in response to determining that the level of confidence is greater than the first predetermined threshold and greater than the second predetermined threshold, outputting, the at least a portion of the cardiac electrogram data, the first indication, and an indication of a high level of confidence that the episode of arrhythmia has occurred in the patient.

Example 13

A method comprising: receiving, by a computing device comprising processing circuitry and a storage medium, cardiac electrogram data sensed by a medical device; receiving, from the user, a selection of an arrhythmia type; applying, by the computing device, a machine learning model, trained using cardiac electrogram data for a plurality of patients, to the received cardiac electrogram data to: determine, based on the machine learning model, that an episode of arrhythmia of the selected type has occurred in the patient; and determine a level of confidence in the determination that the episode of arrhythmia of the selected type has occurred in the patient; and outputting, by the computing device and for display to a user, at least a portion of the cardiac electrogram data, a first indication that the episode of arrhythmia of the selected type has occurred in the patient, and a second indication of the level of confidence that the episode of arrhythmia of the selected type has occurred in the patient.

Example 14

The method of example 13, wherein the at least a portion of the cardiac electrogram data comprises an electrocardiogram (ECG) waveform.

Example 15

The method of example 14, wherein the first indication that the episode of arrhythmia has occurred in the patient comprises an annotation to the ECG waveform.

Example 16

The method of any of examples 13 through 15, wherein the second indication comprises one or more of a color, an image, a light, a sound, or a textual notification.

Example 17

The method of any of examples 13 through 16, wherein the method further comprises determining, by the computing device, that the user is a basic user, wherein, outputting the at least a portion of the cardiac electrogram data, the first indicator that the episode of arrhythmia has occurred in the patient, and the second indicator of the level of confidence that the episode of arrhythmia has occurred in the patient comprises outputting, in response to determining that the user is a basic user, the first indicator that the episode of arrhythmia has occurred in the patient, the second indicator of the level of confidence that the episode of arrhythmia has occurred in the patient, and one or more of: an electrocardiogram (ECG) waveform of the patient; a first representation of a first ECG waveform presenting an episode of arrhythmia; and a second representation of a second ECG waveform presenting normal cardiac behavior.

Example 18

The method any of examples 13 through 16: wherein the method further comprises determining, by the computing device, that the user is an advanced user, wherein, outputting the at least a portion of the cardiac electrogram data, the first indicator that the episode of arrhythmia has occurred in the patient, and the second indicator of the level of confidence that the episode of arrhythmia has occurred in the patient comprises outputting, in response to determining that the user is an advanced user, the first indicator that the episode of arrhythmia has occurred in the patient, the second indicator of the level of confidence that the episode of arrhythmia has occurred in the patient, and one or more of: an electrocardiogram (ECG) waveform of the patient; a start time of the episode of arrhythmia; a stop time of the episode of arrhythmia; a mean R-R interval of the patient during the episode of arrhythmia; an R-R variation of the patient during the episode of arrhythmia; a baseline R-R interval of the patient; a P-wave of the patient during the episode of arrhythmia; a baseline P-wave of the patient; and a morphology variation of the patient.

Example 19

The method of any of examples 13 through 18, wherein the episode of arrhythmia in the patient is at least one of an episode of bradycardia, tachycardia, atrial fibrillation, ventricular fibrillation, or AV Block.

Example 20

The method of any of examples 13 through 19, wherein the machine learning model trained using cardiac electrogram data for the plurality of patients comprises a machine learning model trained using a plurality of electrocardiogram (ECG) waveforms, each ECG waveform labeled with one or more episodes of arrhythmia in a patient of the plurality of patients.

Example 21

The method of any of examples 13 through 20, wherein applying the machine learning model to the received cardiac electrogram data comprises applying the machine learning model to at least one of: electrocardiogram (ECG) data of the patient; the characteristics correlated to arrhythmia in the patient; a type of the arrhythmia in the patient; an activity level of the implantable medical device; an input impedance of the implantable medical device; or a battery level of the implantable medical device.

Example 22

The method of any of examples 1 through 21, wherein outputting the at least a portion of the cardiac electrogram data comprises: identifying a subsection of an electrocardiogram (ECG) of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods; and outputting the subsection of the ECG.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:
1. A computing device comprising:
a storage medium; and
processing circuitry operably coupled to the storage medium and configured to:
receive, from an implantable cardiac monitoring device, electrocardiogram (ECG) data sensed by the implantable cardiac monitoring device;
after receiving the ECG data from the implantable cardiac monitoring device, receive from a user an indication of an arrhythmia of a particular type;

apply a machine learning model, trained using cardiac electrogram data for a plurality of patients, to the received ECG data to:
    determine, based on the machine learning model, that an episode of arrhythmia of the particular type has occurred in a patient; and
    determine a level of confidence in the determination that the episode of arrhythmia of the particular type has occurred in the patient; and
output, for display to the user, at least a portion of the received ECG data identified by the machine learning model as being indicative that the episode of arrhythmia of the particular type has occurred, a first indication that the episode of arrhythmia of the particular type has occurred in the patient, and a second indication of the level of confidence determined by the machine learning model.

2. The computing device of claim 1,
wherein the at least a portion of the received ECG data comprises an ECG waveform, and
wherein the first indication that the episode of arrhythmia has occurred in the patient comprises an annotation to the ECG waveform.

3. The computing device of claim 1, wherein the second indication comprises one or more of a color, an image, a light, a sound, or a textual notification.

4. The computing device of claim 1, wherein the processing circuitry is configured to:
determine that the user is a basic user;
to output the at least a portion of the received ECG data, the first indication that the episode of arrhythmia has occurred in the patient, and the second indication of the level of confidence that the episode of arrhythmia has occurred in the patient, output, in response to determining that the user is a basic user, the first indication that the episode of arrhythmia has occurred in the patient, the second indication of the level of confidence that the episode of arrhythmia has occurred in the patient, and one or more of:
an ECG waveform of the patient;
a first representation of a first ECG waveform presenting an episode of arrhythmia; and
a second representation of a second ECG waveform presenting normal cardiac behavior.

5. The computing device of claim 1, wherein the processing circuitry is configured to:
determine that the user is an advanced user;
to output the at least a portion of the received ECG data, the first indication that the episode of arrhythmia has occurred in the patient, and the second indication of the level of confidence that the episode of arrhythmia has occurred in the patient, output, in response to determining that the user is an advanced user, the first indication that the episode of arrhythmia has occurred in the patient, the second indication of the level of confidence that the episode of arrhythmia has occurred in the patient, and one or more of:
an ECG waveform of the patient;
a start time of the episode of arrhythmia;
a stop time of the episode of arrhythmia;
a mean R-R interval of the patient during the episode of arrhythmia;
an R-R variation of the patient during the episode of arrhythmia;
a baseline R-R interval of the patient;
a P-wave of the patient during the episode of arrhythmia;
a baseline P-wave of the patient; and
a morphology variation of the patient.

6. The computing device of claim 1, wherein the episode of arrhythmia in the patient is at least one of an episode of bradycardia, tachycardia, atrial fibrillation, ventricular fibrillation, or AV Block.

7. The computing device of claim 1, wherein the machine learning model trained using cardiac electrogram data for the plurality of patients comprises a machine learning model trained using a plurality of ECG waveforms, each ECG waveform labeled with one or more episodes of arrhythmia in a patient of the plurality of patients.

8. The computing device of claim 1, wherein to apply the machine learning model to the received ECG data, the processing circuitry is configured to apply the machine learning model to at least one of:
ECG data of the patient;
characteristics correlated to arrhythmia in the patient;
a type of the arrhythmia in the patient;
an activity level of the implantable cardiac monitoring device;
an input impedance of the implantable cardiac monitoring device; or
a battery level of the implantable cardiac monitoring device.

9. The computing device of claim 1, wherein to output the at least a portion of the received ECG data, the processing circuitry is further configured to:
identify a subsection of an the received ECG of the patient, wherein the subsection comprises ECG data for a first time period prior to the episode of arrhythmia, a second time period during the episode of arrhythmia, and a third time period after the episode of arrhythmia, and wherein a length of time of the received ECG data is greater than the first, second, and third time periods; and
output the subsection of the received ECG.

10. The computing device of claim 1, wherein the processing circuitry is further configured to:
in response to determining that the level of confidence determined by the machine learning model is greater than a first predetermined threshold and less than a second predetermined threshold, output the portion of the cardiac electrogram data identified by the machine learning model as being indicative that the episode of arrhythmia of the particular type has occurred with a first visualization technique; and
in response to determining that the level of confidence determined by the machine learning model is greater than the second predetermined threshold, output the portion of the cardiac electrogram data identified by the machine learning model as being indicative that the episode of arrhythmia of the particular type has occurred with a second visualization technique.

11. A method of operating a computing device comprising:
receiving, by a computing device from an implantable cardiac monitoring device, electrocardiogram (ECG) data sensed by the implantable cardiac monitoring device;
after receiving the ECG data from the implantable cardiac monitoring device, receiving, by the computing device, from a user an indication of an arrhythmia of a particular type;
applying, by the computing device, a machine learning model, trained using cardiac electrogram data for a plurality of patients, to the received ECG data sensed by the implantable cardiac monitoring device to:

determine, based on the machine learning model, that an episode of arrhythmia of the particular type has occurred in a patient; and determine a level of confidence in the determination that the episode of arrhythmia of the particular type has occurred in the patient; and outputting at least a portion of the received ECG data identified by the machine learning model as being indicative that the episode of arrhythmia of the particular type has occurred, a first indication that the episode of arrhythmia of the particular type has occurred in the patient, and a second indication of the level of confidence determined by the machine learning model.

12. The method of claim 11,
wherein the at least a portion of the received ECG data comprises an ECG waveform,
wherein the first indication that the episode of arrhythmia has occurred in the patient comprises an annotation to the ECG waveform.

13. The method of claim 11, wherein the second indication comprises one or more of a color, an image, a light, a sound, or a textual notification.

14. The method of claim 11,
wherein the method further comprises determining that the user is a basic user,
wherein, outputting the at least a portion of the received ECG data, the first indication that the episode of arrhythmia has occurred in the patient, and the second indication of the level of confidence that the episode of arrhythmia has occurred in the patient comprises outputting, in response to determining that the user is a basic user, the first indication that the episode of arrhythmia has occurred in the patient, the second indication of the level of confidence that the episode of arrhythmia has occurred in the patient, and one or more of:
an ECG waveform of the patient;
a first representation of a first ECG waveform presenting an episode of arrhythmia; and
a second representation of a second ECG waveform presenting normal cardiac behavior.

15. The method claim 11:
wherein the method further comprises determining that the user is an advanced user,
wherein, outputting the at least a portion of the received ECG data, the first indicator that the episode of arrhythmia has occurred in the patient, and the second indicator of the level of confidence that the episode of arrhythmia has occurred in the patient comprises outputting, in response to determining that the user is an advanced user, the first indicator that the episode of arrhythmia has occurred in the patient, the second indicator of the level of confidence that the episode of arrhythmia has occurred in the patient, and one or more of:
an ECG waveform of the patient;
a start time of the episode of arrhythmia;
a stop time of the episode of arrhythmia;
a mean R-R interval of the patient during the episode of arrhythmia;
an R-R variation of the patient during the episode of arrhythmia;
a baseline R-R interval of the patient;
a P-wave of the patient during the episode of arrhythmia;
a baseline P-wave of the patient; and
a morphology variation of the patient.

16. The method of claim 11, wherein the episode of arrhythmia in the patient is at least one of an episode of bradycardia, tachycardia, atrial fibrillation, ventricular fibrillation, or AV Block.

17. The method of claim 11, wherein the machine learning model trained using cardiac electrogram data for the plurality of patients comprises a machine learning model trained using a plurality of ECG waveforms, each ECG waveform labeled with one or more episodes of arrhythmia in one of the plurality of patients.

18. The method of claim 11, wherein applying the machine learning model to the received ECG data comprises applying the machine learning model to at least one of:
ECG data of the patient;
characteristics correlated to arrhythmia in the patient;
a type of the arrhythmia in the patient;
an activity level of the implantable cardiac monitoring device;
an input impedance of the implantable cardiac monitoring device; or
a battery level of the implantable cardiac monitoring device.

19. The method of claim 11, wherein outputting the at least a portion of the received ECG data comprises:
identifying a subsection of the received ECG data, wherein the subsection comprises ECG data for a first time period prior to the episode of arrhythmia, a second time period during the episode of arrhythmia, and a third time period after the episode of arrhythmia, and wherein a length of time of the received ECG data is greater than the first, second, and third time periods; and
outputting the subsection of the received ECG data.

20. A medical system comprising:
an implantable cardiac monitoring device configured to sense cardiac electrogram data; and
processing circuitry operably coupled to a storage medium and configured to:
receive, from the implantable cardiac monitoring device, the cardiac electrogram data sensed by the implantable cardiac monitoring device;
after receiving the cardiac electrogram data from the implantable cardiac monitoring device, receive from a user an indication of an arrhythmia of a particular type;
apply a machine learning model, trained using cardiac electrogram data for a plurality of patients, to the received cardiac electrogram data to:
determine, based on the machine learning model, that an episode of arrhythmia of a particular type has occurred in a patient; and
determine a level of confidence in the determination that the episode of arrhythmia of the particular type has occurred in the patient; and
output, for display to the user, at least a portion of the cardiac electrogram data identified by the machine learning model as being indicative that the episode of arrhythmia of the particular type has occurred, a first indication that the episode of arrhythmia of the particular type has occurred in the patient, and a second indication of the level of confidence determined by the machine learning model.

21. The medical system of claim 20,
wherein the at least a portion of the cardiac electrogram data comprises an electrocardiogram (ECG) waveform, and wherein the first indication that the episode of arrhythmia has occurred in the patient comprises an annotation to the ECG waveform.

22. The medical system of claim 20, wherein the episode of arrhythmia in the patient is at least one of an episode of bradycardia, tachycardia, atrial fibrillation, ventricular fibrillation, or AV Block.

23. The medical system of claim 20, wherein the machine learning model trained using cardiac electrogram data for the plurality of patients comprises a machine learning model trained using a plurality of electrocardiogram (ECG) waveforms, each ECG waveform labeled with one or more episodes of arrhythmia in one of the plurality of patients.

24. The medical system of claim 20, wherein to output the at least a portion of the cardiac electrogram data, the processing circuitry is further configured to:
  identify a subsection of an electrocardiogram (ECG) of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods; and
  output the subsection of the ECG.

25. The medical system of claim 20, wherein the processing circuitry comprises processing circuitry of a computing device configured to communicate with the implantable cardiac monitoring device.

26. The medical system of claim 20, wherein the processing circuitry comprises processing circuitry of a cloud-based computing device.

27. A medical system comprising:
  an implantable cardiac monitoring device configured to sense cardiac electrogram data; and
  processing circuitry operably coupled to a storage medium and configured to:
    receive, from the implantable cardiac monitoring device, the cardiac electrogram data sensed by the implantable cardiac monitoring device;
    after receiving the cardiac electrogram data from the implantable cardiac monitoring device, receive from a user an indication of an arrhythmia of a particular type;
    output, for display to the user, at least a portion of the cardiac electrogram data, a first indication that an episode of arrhythmia of the particular type has occurred in a patient, and a second indication of a level of confidence that the episode of arrhythmia of the particular type has occurred in the patient; and
  means for applying a machine learning model, trained using cardiac electrogram data for a plurality of patients, to the received cardiac electrogram data to:
    determine, based on the machine learning model, that the episode of arrhythmia of the particular type has occurred in the patient; and
    determine the level of confidence in the determination that the episode of arrhythmia of the particular type has occurred in the patient.

28. The medical system of claim 27,
  wherein the at least a portion of the cardiac electrogram data comprises an electrocardiogram (ECG) waveform, and
  wherein the first indication that the episode of arrhythmia has occurred in the patient comprises an annotation to the ECG waveform.

29. The medical system of claim 27, wherein the episode of arrhythmia in the patient is at least one of an episode of bradycardia, tachycardia, atrial fibrillation, ventricular fibrillation, or AV Block.

30. The medical system of claim 27, wherein the machine learning model trained using cardiac electrogram data for the plurality of patients comprises a machine learning model trained using a plurality of electrocardiogram (ECG) waveforms, each ECG waveform labeled with one or more episodes of arrhythmia in one of the plurality of patients.

31. The medical system of claim 27, wherein to output the at least a portion of the cardiac electrogram data, the processing circuitry is further configured to:
  identify a subsection of an electrocardiogram (ECG) of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods; and
  output the subsection of the ECG.

* * * * *